(12) United States Patent
Wu et al.

(10) Patent No.: US 12,152,271 B2
(45) Date of Patent: Nov. 26, 2024

(54) METHODS AND COMPOSITIONS FOR PREPARING POLYNUCLEOTIDES

(71) Applicant: CYGNUS BIOSCIENCES (BEIJING) CO., LTD., Beijing (CN)

(72) Inventors: Yalei Wu, Foster City, CA (US); Wai Ho Lee, San Francisco, CA (US); Genhua Zheng, Fremont, CA (US); Kai Qin Lao, Pleasanton, CA (US)

(73) Assignee: CYGNUS BIOSCIENCES (BEIJING) CO., LTD, Beijing (CN)

( * ) Notice: Subject to any disclaimer, the term of this patent is extended or adjusted under 35 U.S.C. 154(b) by 1066 days.

(21) Appl. No.: 17/050,823

(22) PCT Filed: Apr. 25, 2019

(86) PCT No.: PCT/US2019/029100
§ 371 (c)(1),
(2) Date: Oct. 26, 2020

(87) PCT Pub. No.: WO2019/210049
PCT Pub. Date: Oct. 31, 2019

(65) Prior Publication Data
US 2021/0230666 A1    Jul. 29, 2021

Related U.S. Application Data

(60) Provisional application No. 62/663,967, filed on Apr. 27, 2018.

(51) Int. Cl.
C12Q 1/6806    (2018.01)
C12Q 1/6869    (2018.01)

(52) U.S. Cl.
CPC ......... *C12Q 1/6806* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 5,234,809 A | 8/1993 | Boom et al. | |
| 5,235,809 A | 8/1993 | Farrell | |
| 5,705,628 A | 1/1998 | Hawkins | |
| 6,210,891 B1 | 4/2001 | Nyren et al. | |
| 2011/0318739 A1 | 12/2011 | Santourlidis | |
| 2013/0217071 A1 | 8/2013 | Montesclaros et al. | |

(Continued)

FOREIGN PATENT DOCUMENTS

| WO | WO-2012061832 A1 * | 5/2012 | ......... C12N 15/1065 |
|---|---|---|---|
| WO | WO-2014015084 A2 | 1/2014 | |

(Continued)

OTHER PUBLICATIONS

Brenner. A cultivated taste for yeast. Genome Biol. 2000;1(1):Reviews103. Epub Apr. 27, 2000.

(Continued)

*Primary Examiner* — Kaijiang Zhang
(74) *Attorney, Agent, or Firm* — NKL Law; Allen Xue

(57) ABSTRACT

Provided herein are methods, compositions, and kits for forming amplification products. In various embodiments provided herein, transposomes comprising transposases are used in forming tagged polynucleotides for downstream amplification and polynucleotide processing steps.

19 Claims, 7 Drawing Sheets

Specification includes a Sequence Listing.

(56) References Cited

U.S. PATENT DOCUMENTS

2014/0135234 A1    5/2014    Williams et al.
2014/0363815 A1    12/2014    Dahl et al.
2015/0299767 A1    10/2015    Armour et al.

FOREIGN PATENT DOCUMENTS

WO    WO-2015089333 A1    6/2015
WO    WO-2016061517 A2    4/2016
WO    WO-2016101258 A1    6/2016

OTHER PUBLICATIONS

Brenner, C. Chemical genomics in yeast. Genome Biology. 2004; 5:240.

Dicker, et al. The detection of TP53 mutations in chronic lymphocytic leukemia independently predicts rapid disease progression and is highly correlated with a complex aberrant karyotype. Leukemia. Jan. 2009; 23(1):117-124.

Eason, et al. Characterization of synthetic DNA bar codes in *Saccharomyces cerevisiae* gene-deletion strains. Proc Natl Acad Sci U S A. Jul. 27, 2004;101(30):11046-51. Epub Jul. 16, 2004.

Giaever, et al. Chemogenomic profiling: identifying the functional interactions of small molecules in yeast. Proc Natl Acad Sci U S A. Jan. 20, 2004;101(3):793-8. Epub Jan. 12, 2004.

International search report with written opinion dated Apr. 3, 2019 for PCT/US2018/052217.

Kumar et al., Emerging technologies in yeast genomics. Nature Reviews Genetics 2: 302-312 (2001).

McLendon, et al. Survival analysis of presumptive prognostic markers among oligodendrogliomas. John Wiley & Sons. Oct. 15, 2005; 104(8):1693-1699.

Miller et al. A Simple salting out procedure for extracting DNA from human nucleated cells. Nucleic Acids Research vol. 16, No. 3, 1215 (1988).

PCT/US2018/052217 International Preliminary Report on Patentability dated Mar. 24, 2020.

PCT/US2019/041121 International Preliminary Report on Patentability dated Jan. 21, 2021.

Winzeler, et al. Functional characterization of the S. cerevisiae genome by gene deletion and parallel analysis. Science. Aug. 6, 1999;285(5429):901-6.

\* cited by examiner

SEQUENCE LISTING

<160> NUMBER OF SEQ ID NOS: 4

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtaggtgtga gtgatggttg aggtagtaga tgtgtataag agacag                    46

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgtctctta tacacatct                                                  19

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 3
gtgagtgatg gttgaggtag tgtggagaga tgtgtataag agacag          46

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agatgtgtat aagagacag                                         19
```

METHODS AND COMPOSITIONS FOR PREPARING POLYNUCLEOTIDES

CROSS REFERENCE TO RELATED APPLICATIONS

The present application claims priority to U.S. Provisional Application Ser. No. 62/663,967, filed Apr. 27, 2018, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 23, 2019, is named 53081-702_601_SL.txt and is 1,176 bytes in size.

BACKGROUND

Transposase-mediated fragmentation and tagging of polynucleotides can be used in the preparation of polynucleotides, for example in the generation of sequencing libraries. Tagmentation offers advantages of simplified sample preparation and work-flow in which polynucleotides to be sequenced can be fragmented and tagged in a single reaction. These resulting polynucleotides can be further amplified and/or subjected to sequence specific selection prior to sequencing. Sequence information of polynucleotides can be used to identify sequence variants for diagnostic, therapeutic, forensic, and many other applications.

Simple and rapid sample preparation can be useful for analyzing polynucleotide samples. Polynucleotide samples can be processed in parallel or in bulk, for example, in a high-throughput multiplexing. However, the existing methods of preparing nucleic acid samples often suffer from a number of drawbacks. Amongst them are low yields and requirements of high amounts of starting material.

SUMMARY

In view of the foregoing, there is a need for improved methods for processing polynucleotides. The methods, compositions, reaction mixtures, and kits provided herein address this need, and provide additional advantages as well.

In an aspect, the present disclosure provides a method of characterizing a polynucleotide in a sample. The method comprises (a) contacting a double-stranded polynucleotide in a sample with a first set of transposome complexes, the first set comprising transposome complexes having a first transposon sequence, to generate a first plurality of overhang fragments that comprise the first transposon sequence at a 5' end; (b) subjecting the first plurality of overhang fragments to an extension reaction to generate a first plurality of blunt-ended fragments; (c) conducting a primer-directed extension reaction with a primer comprising the first transposon sequence or a portion thereof to generate copies of the first plurality of blunt-ended fragments or fragments thereof; (d) contacting the first plurality of blunt-ended fragments or fragments thereof with a second set of transposome complexes, the second set comprising transposome complexes having a second transposon sequence, to generate a second plurality of overhang fragments that comprise the second transposon sequence at a 5' end; (e) subjecting the second plurality of overhang fragments to an additional extension reaction to generate a second plurality of blunt-ended fragments; and (f) generating sequence reads from the second plurality of blunt-ended fragments or derivatives thereof, thereby characterizing the double-stranded polynucleotide in the sample. In some embodiments, the first transposon sequence and the second transposon sequence are not identical. In some embodiments, the second set further comprises transposome complexes having the first transposon sequence. In some embodiments, the second set further comprises transposome complexes having a third transposon sequence.

In an aspect, the present disclosure provides a method of characterizing a polynucleotide in a sample, comprising: (a) contacting a double-stranded polynucleotide in a sample with a first set of transposome complexes, individual transposome complexes of the first set comprising a first transposon sequence, to generate a first plurality of overhang fragments that comprise the first transposon sequence at a 5' end; (b) subjecting the first plurality of overhang fragments to an extension reaction to generate a first plurality of blunt-ended fragments; (c) conducting a primer-directed extension reaction with a primer comprising the first transposon sequence or a portion thereof to generate copies of the first plurality of blunt-ended fragments or fragments thereof; (d) contacting the first plurality of blunt-ended fragments or fragments thereof with a second set of transposome complexes, individual transposome complexes of the second set comprising a second transposon sequence, to generate a second plurality of overhang fragments that comprise the second transposon sequence at a 5' end, wherein the first set of transposome complexes and the second set of transposome complexes are different in that: (i) transposon sequences comprised therein are distinct between the first and the second sets of transposome complexes; and/or (ii) one set of the transposome complexes utilized in step (a) or (d) are homodimer transposomes and one other set of the transposome complexes utilized are heterodimer transposomes; (e) subjecting the second plurality of overhang fragments to an additional extension reaction to generate a second plurality of blunt-ended fragments; and (f) generating sequence reads from the second plurality of blunt-ended fragments or derivatives thereof, thereby characterizing the double-stranded polynucleotide in the sample. In some embodiments, the first set of transposome complexes and the second set of transposome complexes are different in that transposon sequences comprised therein are distinct between the first and the second sets of the transposome complexes. In some embodiments, the first set of transposome complexes and the second set of transposome complexes are different in that one set of the transposome complexes utilized in step (a) or (d) are homodimer transposomes and one other set of transposome complexes utilized are heterodimer transposomes.

In some embodiments, step (d) comprises contacting the first plurality of blunt-ended fragments or fragments thereof with at least two additional sets of transposome complexes, wherein individual sets of the additional sets of transposome complexes comprise homodimer transposomes, and wherein transposon sequences across the individual sets are unique.

In some embodiments, double-stranded polynucleotide comprises genomic DNA. In some embodiments, the genomic DNA is from a single cell. In some embodiments, the double-stranded polynucleotide comprises a chromosome. In some embodiments, the double-stranded polynucleotide is from a single cell.

In some embodiments, characterizing the double-stranded polynucleotide yields haplotype information. In some embodiments, characterizing the double-stranded polynucleotide comprises identifying a structural variation in the polynucleotide, wherein the structural variation is a copy number variation (CNV), an insertion, a deletion, a translocation, a retrotransposon, an inversion, a rearrangement, a repeat expansion, or a duplication.

In some embodiments, the double-stranded polynucleotide is at least about 1 megabase (Mb) in length.

In some embodiments, the first plurality of blunt-ended fragments comprises fragments of at least about 500 bases in length.

In some embodiments, the second plurality of blunt-ended fragments comprises fragments of at least about 100 bases in length.

In some embodiments, individual single-stranded polynucleotides of the first plurality of blunt-ended fragments form a stem-loop structure. In some embodiments, the stem-loop structure comprises a stem of at least 10 base pairs in length. In some embodiments, the stem of the stem-loop structure has a melting temperature (Tm) of at least 50° C.

In some embodiments, the method further comprises attaching sequencing adaptors to the second plurality of blunt-ended fragments to yield the derivatives thereof.

In some embodiments, individual transposome complexes of the first set and/or the second set comprise a transposase selected from Tn transposase, MuA transposase, and Vibhar transposase. In some embodiments, the transposase is a Tn transposase selected from Tn3, Tn5, Tn7, and Tn10.

In an aspect, the present disclosure provides a method for identifying a low frequency allele. The method comprises (a) contacting a double-stranded polynucleotide with transposome complexes, individual transposome complexes comprising a transposon sequence, to generate a plurality of overhang fragments that comprise the transposon sequence at a 5' end; (b) subjecting the plurality of overhang fragments to an extension reaction to generate a plurality of blunt-ended fragments; (c) conducting a first primer-directed extension reaction with a primer comprising the transposon sequence or a portion thereof and a first barcode sequence (X1) to generate a first plurality of barcoded polynucleotides comprising the first barcode sequence (X1) at a 5' end; (d) conducting a second primer-directed extension with a primer comprising the transposon sequence or a portion thereof and a second barcode sequence (X2) to generate a second plurality of barcoded polynucleotides comprising the second barcode sequence (X2) at a 5' end and a reverse complement of the first barcode sequence (X1') at a 3' end; (e) generating sequence reads from the second plurality of barcoded polynucleotides or derivatives thereof to yield a plurality of sequence reads; and (f) identifying a low frequency allele in the double-stranded polynucleotide when the low frequency allele occurs in sequence reads of both a sense strand and an antisense strand of the double-stranded polynucleotide, wherein (i) sequence reads comprising, from 5' end to 3' end, (a) X2, the sense strand sequence, and X1' or (b) X1, the antisense strand sequence, and a reverse complement of X2 (X2'), are identified as originating from the sense strand of the double-stranded polynucleotide, and (ii) sequence reads comprising, from a 5' end to 3' end, (a) X1, the sense strand sequence, and X2' or (b) X2, the antisense strand sequence, and X1', are identified as originating from the antisense strand of the double-stranded polynucleotide.

In an aspect, the present disclosure provides a method for identifying a sequence variant. The method comprises (a) contacting a double-stranded polynucleotide with transposome complexes, individual transposome complexes comprising a transposon sequence, to generate a plurality of overhang fragments that comprise the transposon sequence at a 5' end; (b) subjecting the plurality of overhang fragments to an extension reaction to generate a plurality of blunt-ended fragments; (c) conducting a first primer-directed extension reaction with a primer comprising the transposon sequence or a portion thereof and a first barcode sequence (X1) to generate a first plurality of barcoded polynucleotides comprising the first barcode sequence (X1) at a 5' end; (d) conducting a second primer-directed extension with a primer comprising the transposon sequence or a portion thereof and a second barcode sequence (X2) to generate a second plurality of barcoded polynucleotides comprising the second barcode sequence (X2) at a 5' end and a reverse complement of the first barcode sequence (X1') at a 3' end; (e) generating sequence reads from the second plurality of barcoded polynucleotides or derivatives thereof to yield a plurality of sequence reads; and (f) identifying a sequence variant in the double-stranded polynucleotide compared to a reference sequence when the sequence variant occurs in sequence reads of both a sense strand and an antisense strand of the double-stranded polynucleotide, wherein (i) sequence reads comprising, from 5' end to 3' end, (a) X2, the sense strand sequence, and X1' or (b) X1, the antisense strand sequence, and a reverse complement of X2 (X2'), are identified as originating from the sense strand of the double-stranded polynucleotide, and (ii) sequence reads comprising, from a 5' end to 3' end, (a) X1, the sense strand sequence, and X2' or (b) X2, the antisense strand sequence, and X1', are identified as originating from the antisense strand of the double-stranded polynucleotide.

In some embodiments, the double-stranded polynucleotide comprises genomic DNA.

In some embodiments, the genomic DNA is from a single cell. In some embodiments, the double-stranded polynucleotide comprises a chromosome. In some embodiments, the double-stranded polynucleotide comprises cell-free DNA.

In some embodiments, the double-stranded polynucleotide is at least 1 megabase (Mb) in length.

In some embodiments, the plurality of blunt-ended fragments comprises fragments at least 100 bases in length.

In some embodiments of the methods herein, the method further comprises attaching sequencing adaptors to the second plurality of barcoded polynucleotides to yield the derivatives thereof.

In some embodiments, individual transposome complexes comprise a transposase selected from Tn transposase, MuA transposase, and Vibhar transposase. In some embodiments, the transposase is a Tn transposase selected from Tn3, Tn5, Tn7, and Tn10.

In some embodiments, an allele frequency of the low frequency allele in a population is less than 5%.

In some embodiments, the low frequency allele is detected with an accuracy of at least 85%.

In some embodiments, the sequence variant represents less than 5% of double-stranded polynucleotides in a nucleic acid sample.

In some embodiments, the sequence variant is detected with an accuracy of at least 85%.

In some embodiments, the nucleic acid sample comprises cell-free polynucleotides.

In some embodiments, the nucleic acid sample is from a single cell.

In an aspect, the present disclosure provides a method of selectively sampling a subset of regions of a polynucleotide. The method comprises (a) contacting a double-stranded polynucleotide with a first set of transposome complexes to generate a first plurality of overhang fragments that comprise a first transposon sequence or a second transposon sequence at the 5' end, wherein the first set of transposome complexes comprises a mixture of (i) homodimer transposases comprising the first transposon sequence, and (ii) homodimer transposases comprising the second transposon sequence; (b) subjecting the first plurality of overhang fragments to an extension reaction to generate a first plurality of blunt-ended fragments; (c) conducting a primer-directed extension reaction with a primer comprising the first transposon sequence or a portion thereof to selectively generate copies of a subset of the first plurality of blunt-ended fragments comprising the first transposon sequence or fragments thereof; (d) contacting the first plurality of blunt-ended fragments comprising the first transposon sequence or fragments thereof with a second set of transposome complexes to generate a second plurality of overhang fragments, wherein the second set of transposome complexes comprises (i) a plurality of homodimer transposases, or (ii) a plurality of heterodimer transposases; (e) subjecting the second plurality of overhang fragments to an additional extension reaction to generate a second plurality of blunt-ended fragments; and (f) generating sequence reads from the second plurality of blunt-ended fragments or derivatives thereof, thereby selectively sampling a subset of regions of the double-stranded polynucleotide. In some embodiments, the second set of transposome complexes comprises a plurality of homodimer transposases. In some embodiments, the second set of transposome complexes comprises a plurality of heterodimer transposases.

In some embodiments, in the mixture of (i) homodimer transposases comprising the first transposon sequence, and (ii) homodimer transposases comprising the second transposon sequence, (i) and (ii) are present at a molar ratio of about 1:9.

In some embodiments, in the mixture of (i) homodimer transposases comprising the first transposon sequence, and (ii) homodimer transposases comprising the second transposon sequence, (i) and (ii) are present at a molar ratio not equal to 1:1.

In some embodiments, the mixture of (a) further comprises (iii) heterodimer transposases comprising the first transposon sequence and the second transposon sequence. In some embodiments, in the mixture of (i) homodimer transposases comprising the first transposon sequence, (ii) homodimer transposases comprising the second transposon sequence, and (iii) heterodimer transposases comprising the first transposon sequence and the second transposon sequence, a molar concentration of (i) is less than that of (ii) and (iii). In some embodiments, in the mixture of (i) homodimer transposases comprising the first transposon sequence, (ii) homodimer transposases comprising the second transposon sequence, and (iii) heterodimer transposases comprising the first transposon sequence and the second transposon sequence, a molar concentration of (ii) is less than that of (i) and (iii).

In some embodiments, in the mixture of (i) homodimer transposases comprising the first transposon sequence, (ii) homodimer transposases comprising the second transposon sequence, and (iii) heterodimer transposases comprising the first transposon sequence and the second transposon sequence, a molar concentration of (iii) is less than that of (i) and (ii).

In some embodiments, the first plurality of overhang fragments comprises (i) fragments comprising the first transposon sequence, (ii) fragments comprising the second transposon sequence, and (iii) fragments comprising both the first and second transposon sequence, and a molar concentration of (i) is less than that of (ii) and (iii).

In some embodiments, the double-stranded polynucleotide comprises genomic DNA.

In some embodiments, the genomic DNA is from a single cell. In some embodiments, the double-stranded polynucleotide comprises a chromosome. In some embodiments, the double-stranded polynucleotide is from a single cell.

In some embodiments, the double-stranded polynucleotide is at least 1 megabase (Mb) in length.

In some embodiments, the first plurality of blunt-ended fragments comprises fragments at least 500 bases in length.

In some embodiments, the second plurality of blunt-ended fragments comprises fragments at least 100 bases in length.

In some embodiments, the single-stranded polynucleotides of the first plurality of blunt-ended fragments comprising (i) the first transposon sequence at a 5' end and a reverse complement of the first transposon sequence at a 3' end, or (ii) the second transposon sequence at a 5' end and a reverse complement of the second transposon sequence at a 3' end, form a stem-loop structure. In some embodiments, the stem-loop structure comprises a stem of at least 10 base pairs in length. In some embodiments, the stem of the stem-loop structure has a melting temperature (Tm) of at least 50° C.

In some embodiments of the various methods herein, the method further comprises attaching sequencing adaptors to the second plurality of blunt-ended fragments to yield the derivatives.

In some embodiments, individual transposome complexes of the first set and/or the second set comprise a transposase selected from Tn transposase, MuA transposase, and Vibhar transposase. In some embodiments, the transposase is a Tn transposase selected from Tn3, Tn5, Tn7, and Tn10.

In an aspect, the present disclosure provides compositions for carrying out any of the various embodiments provided herein. In some embodiments, a composition comprises a mixture of (i) homodimer transposases comprising a first transposon sequence and (ii) homodimer transposases comprising a second transposon sequence. In some embodiments, (i) and (ii) are present at a molar ratio of about 1:9. In some embodiments, (i) and (ii), are present at a molar ratio not equal to 1:1.

In some embodiments, the composition further comprises (iii) heterodimer transposases comprising the first transposon sequence and the second transposon sequence. In some embodiments, a molar concentration of (i) is less than that of (ii) and (iii). In some embodiments, a molar concentration of (ii) is less than that of (i) and (iii). In some embodiments, a molar concentration of (iii) is less than that of (i) and (ii).

In an aspect, a reaction mixture comprises (a) a mixture of (i) homodimer transposases comprising a first transposon sequence and (ii) homodimer transposases comprising a second transposon sequence; and (b) a double-stranded polynucleotide comprising genomic DNA. In some embodiments, the reaction mixture further comprises (iii) heterodimer transposases comprising the first transposon sequence and the second transposon sequence.

In some embodiments, the genomic DNA is from a single cell. In some embodiments, genomic DNA is a single chromosome.

In an aspect, the present disclosure provides a kit for carrying out any of the various embodiments provided herein. In some embodiments, a kit comprises: (a) a first set of transposome complexes, individual transposome complexes of the first set comprising a first transposon sequence; (b) a primer comprising the first transposon sequence or a portion thereof; (c) a second set of transposome complexes, individual transposome complexes of the second set comprising a second transposon sequence; and (d) instructions for practicing any of the methods provided herein, wherein the first set of transposome complexes and the second set of transposome complexes are different in that: (i) transposon sequences comprised therein are distinct between the first and the second sets of transposome complexes; and/or (ii) one set of the transposome complexes utilized are homodimer transposomes and one other set of the transposome complexes utilized are heterodimer transposomes.

In some embodiments, a kit comprises: (a) transposome complexes, individual transposome complexes comprising a transposon sequence; (b) a first primer comprising the transposon sequence or a portion thereof and a first barcode sequence (X1); (c) a second primer comprising the transposon sequence or a portion thereof and a second barcode sequence (X2); and (d) instructions for practicing any method provided herein.

In some embodiments, a kit comprises: (a) a first set of transposome complexes comprising: (i) homodimer transposases comprising a first transposon sequence, (ii) homodimer transposases comprising a second transposon sequence, and optionally (iii) heterodimer transposases comprising the first transposon sequence and the second transposon sequence; (b) a primer comprising the first transposon sequence or a portion thereof; (c) a second set of transposome complexes comprising: (i) a plurality of homodimer transposases, or (ii) a plurality of heterodimer transposases; and instructions for practicing any method provided herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments and the accompanying drawings (also "Figure" and "FIG." herein), of which:

DETAILED DESCRIPTION

Figure 1:
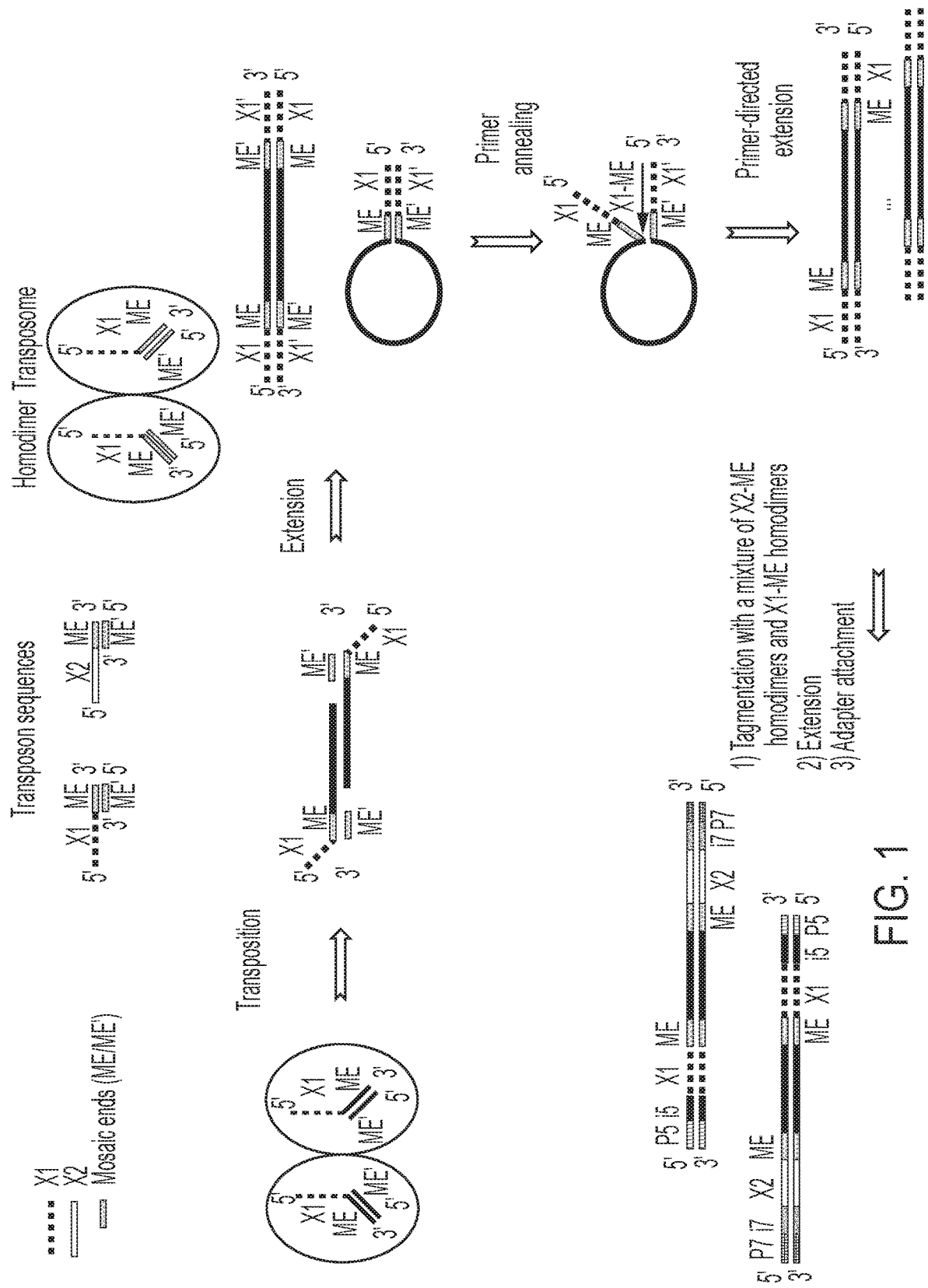
FIG. 1 illustrates a nonlimiting example method of characterizing a polynucleotide.

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The terms "about" and "approximately" mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about," meaning within an acceptable error range for the particular value, should be assumed.

The terms "polynucleotide", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "strand," as used herein, refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands, or the "sense" and "antisense" strands. The assignment of a strand as being a top or bottom strand is arbitrary and does not imply any particular orientation, function or structure.

A polynucleotide may have a 5' end and 3' end, referring to the end-to-end chemical orientation of a single strand of polynucleotide or nucleic acid. In a single strand of linear DNA or RNA, the chemical convention of naming carbon atoms in the nucleotide sugar-ring means that there generally exists a 5' end which frequently contains a phosphate group attached to the 5' carbon and a 3' end which typically is unmodified from the ribose —OH substituent (hydroxyl group). In some cases, a polynucleotide may have a —OH substituent or a hydroxyl group at a 5' end and —P group or phosphate group at a 3' end. A phosphate group attached to the 5'-end permits ligation of two nucleotides, e.g., the covalent binding of a 5'-phosphate to the 3'-hydroxyl group of another nucleotide, to form a phosphodiester bond. Removal of the 5'-phosphate may inhibit or prevent ligation. The 3'-hydroxyl group is also important as it is joined to the 5'-phosphate in ligation.

The term "tag," as used herein, refers to a nucleic acid molecule that provides a means of identifying a polynucleotide to which it is attached. For example, a tag can comprise a polynucleotide sequence that permits identification, recognition, and/or molecular or biochemical manipulation of the target polynucleotide to which it is attached (e.g., by providing a site for annealing an oligonucleotide, such as a primer for extension by a DNA polymerase, or an oligonucleotide for capture or for a ligation reaction). The process of attaching the tag to a polynucleotide molecule is sometimes referred to herein as "tagging" and a polynucleotide that undergoes tagging or that contains a tag is referred to as "tagged" (e.g., "tagged polynucleotide" or "tagged fragment"). For example, a tagged polynucleotide fragment (e.g., tagged fragment) can comprise a transposon having a transposon sequence as a tag.

The term "sequence variant," as used herein, refers to any variation in sequence relative to one or more reference sequences. Typically, the sequence variant occurs with a lower frequency than the reference sequence for a given population of individuals for whom the reference sequence is known. In some cases, the reference sequence is a single known reference sequence, such as the genomic sequence of a single individual. In some cases, the reference sequence is a consensus sequence formed by aligning multiple known sequences, such as the genomic sequence of multiple individuals serving as a reference population, or multiple sequencing reads of polynucleotides from the same individual. In some cases, the sequence variant occurs with a low frequency in the population (also referred to as a "rare" sequence variant). For example, the sequence variant may occur with a frequency of about or less than about 10%, 9%, 8%, 7%, 6%, 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant occurs with a frequency of about or less than about 1%. In some cases, the sequence variant occurs with a frequency of about or less than about 0.1%. A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), insertion and/or deletion polymorphisms (INDEL), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some embodiments, a sequence variant can refer to a chromosome rearrangement, including, but not limited to, a translocation or fusion gene.

The term "allele," as used herein, refers to any one or more alternative forms of a gene at a particular locus, all of which may relate to one trait or characteristic at the specific locus. In a diploid cell of an organism, alleles of a given gene can be located at a specific location, or locus (loci plural) on a chromosome. The sequences at these variant sites that differ between different alleles can be termed "variants," "polymorphisms," or "mutations."

The term "wild-type" when made in reference to an allele or sequence, generally refers to the allele or sequence that encodes the phenotype most common in a particular natural population. In some cases, a wild-type allele can refer to an allele present at highest frequency in the population. In some cases, a wild-type allele or sequence refers to an allele or sequence associated with a normal state relative to an abnormal state, for example a disease state.

The terms "mutant" or "variant," when made in reference to an allele or sequence, generally refer to an allele or sequence that does not encode the phenotype most common in a particular natural population. In some cases, a mutant allele can refer to an allele present at a lower frequency in a population relative to the wild-type allele. In some cases, a mutant allele or sequence can refer to an allele or sequence mutated from a wild-type sequence to a mutant sequence that presents a phenotype associated with a disease state. Mutant alleles and sequences may be different from wild-type alleles and sequences by only one base, but can be different up to several bases. The term mutant when made in reference to a gene generally refers to one or more sequence mutations in the gene, including a point mutation, a single nucleotide polymorphism (SNP), an insertion, a deletion, a substitution, a transposition, a translocation, a copy number variation, another genetic mutation, alternation, or sequence variation.

The terms "allele frequency" or "frequency" when used with reference to allele, as used herein, generally refer to the relative frequency of an allele (e.g., variant of a gene) in a sample, e.g., expressed as a fraction or percentage. In some cases, allele frequency may refer to the relative frequency of an allele (e.g., variant of a gene) in a sample, such as a cell-free nucleic acid sample or genomic DNA sample. In some cases, allele frequency may refer to the relative frequency of an allele (e.g., variant of a gene) in a sample. In an example, a genetic locus can comprise allele A or allele B. If allele A and allele B are present in a nucleic acid sample at similar concentrations, the allelic frequency of both alleles may be about 50%. If, for every copy of allele A, a nucleic acid sample comprises 9 copies of allele B, the allelic frequency of A may be about 10% and the allelic frequency of B may be about 90%.

The term "haplotype," as used herein, refers to a combination of alleles at multiple loci that are transmitted together on the same chromosome. Haplotype may refer to as few as two loci or to an entire chromosome, depending on the number of recombination events that have occurred between a given set of loci. Haplotype can also refer to a set of single nucleotide polymorphisms (SNPs) on a single chromatid that are statistically associated. The term "haplotypic data," also "phased data" or "ordered genetic data," refers to data from a single chromosome in a diploid or polyploid genome, i.e., either the segregated maternal or paternal copy of a chromosome in a diploid genome. As used herein, "phasing" refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual. The term "phased data" refers to genetic data where the haplotype has been determined.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

The term "overhang fragment," as used herein, refers to a double-stranded polynucleotide, e.g., a fragment of a longer double-stranded polynucleotide, having unpaired nucleotides present at one or both ends of the polynucleotide. In cases where an overhang is not present, the double-stranded polynucleotide may be referred to as having a "blunt-end".

The terms "stem-loop product" and "stem-loop structure", as used herein, generally refer to a secondary structure of a polynucleotide in which intramolecular hybridization occurs between portions of the polynucleotide. A stem loop may form when two regions of a single polynucleotide strand hybridize to form a double-stranded portion, which can be referred to as a "stem," and a single-stranded loop that is unpaired, which can be referred to as a "loop". The stem can be of any variable length of base pairs, and base pairing along a stem may be interrupted internally by gaps of one or more unpaired bases on one or both portions participating in the stem. The loop can be of any variable length of unpaired bases. In some cases, the loop is at least 3 bases in length. In some cases, the two regions forming the "stem" are completely complementary. In some cases, the two regions forming the "stem" are partially complementary. In some cases, a single polynucleotide may comprise one stem loop structure. In some cases, a single polynucleotide may comprise more than one stem loop structure. The stem portion of a stem loop structure may terminate as a double stranded section with no overhangs, with a single stranded section comprising a 5' overhang, with a single stranded section comprising a 3' overhang, or with single-stranded portions extending from both the 5' end and the 3' end. A stem loop structure can also be referred to as a "hairpin" or "hairpin structure."

The terms "adaptor" or "adapter," as used herein, generally refer to a nucleic acid which can be attached to another polynucleotide. For example, an adaptor can refer to a single-stranded polynucleotide which can be attached to a single-stranded polynucleotide (e.g., a cell-free polynucleotide, fragment of a cell-free polynucleotide, genomic DNA, or fragment of genomic DNA). In some cases, an adaptor can refer to a double-stranded nucleic acid which can be attached to another double-stranded nucleic acid (e.g., a cell-free polynucleotide, fragment of a cell-free polynucleotide, genomic DNA, or fragment of genomic DNA). An adaptor can be attached to either a 5' end or a 3' end of a polynucleotide. In some cases, an adaptor can be attached to both ends of a polynucleotide, that is, one adaptor to each end.

The term "primer," as used herein, generally refers to an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension reaction may be determined by the sequence of the template polynucleotide. Usually primers are extended by a DNA polymerase. Primers are generally of a length compatible with their use in synthesis of primer extension products, and usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primers can first be treated to separate its strands before being used to prepare primer extension products, or simply referred to as extension products. This denaturation step can be effectuated by heat, but may alternatively be carried out using alkali, followed by neutralization. Thus, a "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "extension product," as used herein, generally refers to a product of a reaction in which a nucleotide primer is extended by the covalent addition of nucleotides. In some cases, the nucleotide incorporation can be guided by a template. In some cases, the nucleotide incorporation can occur without a template (e.g., "template-independent"). In some cases, an extension product is an amplification product, such as from PCR amplification, rolling circle amplification (RCA), or isothermal amplification.

The terms "amplify," "amplifies," "amplified," and "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation. In some cases, the amplification is effected by means of PCR using a pair of primers. Amplified products can be subjected to subsequent analyses, including but not limited to melting curve analysis, nucleotide sequencing, single-strand conformation polymorphism assay, allele-specific oligonucleotide hybridization, Southern blot analysis, and restriction endonuclease digestion.

The terms "isolated" and "isolating," with reference to a polynucleotide or polynucleotide complex, including but not limited to tagmentation products and extension products, generally refer to a preparation of the substance (e.g., polynucleotide, polynucleotide complex, tagmentation products and extension products thereof) devoid of at least some of the other components that may also be present where the substance or a similar substance naturally occurs or is initially obtained from (e.g., a biological sample, a sample reaction volume, e.g., a tagmentation reaction volume, an extension reaction volume, etc). For example, an isolated substance may be prepared using a purification technique to enrich it from a source mixture. Enrichment can be measured on an absolute basis or in terms of a concentration, for example in terms of weight per volume of solution, molecules per volume of solution, or any other appropriate measure.

In various aspects, the present disclosure provides methods, reaction mixtures, kits, and systems for characterizing and analyzing a polynucleotide. The polynucleotide can be part of a polynucleotide sample. The polynucleotide may be an isolated polynucleotide. The subject methods, reaction mixtures, kits, and systems can be useful for preparing a polynucleotide such as, but not limited to, cell-free DNA and genomic DNA.

Provided herein are methods of characterizing a polynucleotide in a sample. In an aspect, a method of characterizing a polynucleotide in a sample comprises (a) contacting a double-stranded polynucleotide in a sample with a first set of transposome complexes, the first set comprising transposome complexes having a first transposon sequence, to generate a first plurality of overhang fragments that comprise the first transposon sequence at a 5' end; (b) subjecting the first plurality of overhang fragments to an extension reaction to generate a first plurality of blunt-ended fragments; (c) conducting a primer-directed extension reaction with a primer comprising the first transposon sequence or a portion thereof to generate copies of the first plurality of blunt-ended fragments or fragments thereof; (d) contacting the first plurality of blunt-ended fragments or fragments thereof with a second set of transposome complexes, the second set comprising transposome complexes having a second transposon sequence, to generate a second plurality of overhang fragments that comprise the second transposon sequence at a 5' end; (e) subjecting the second plurality of overhang fragments to an additional extension reaction to generate a second plurality of blunt-ended fragments; and (f) generating sequence reads from the second plurality of blunt-ended fragments or derivatives thereof, thereby characterizing the double-stranded polynucleotide in the sample. In some embodiments, the first transposon sequence and the second transposon sequence are not identical. In some embodiments, the second set of transposome complexes further comprises transposome complexes having the first transposon sequence. In some embodiments, the second set of transposome complexes further comprises transposome complexes having a third transposon sequence, a fourth transposon sequence, a fifth transposon sequence, etc.

In an aspect, a method of characterizing a polynucleotide in a sample comprises (a) contacting a double-stranded polynucleotide in a sample with a first set of transposome complexes, individual transposome complexes of the first set comprising a first transposon sequence, to generate a first plurality of overhang fragments that comprise the first transposon sequence at a 5' end; (b) subjecting the first plurality of overhang fragments to an extension reaction to generate a first plurality of blunt-ended fragments; (c) conducting a primer-directed extension reaction with a primer comprising the first transposon sequence or a portion thereof to generate copies of the first plurality of blunt-ended fragments or fragments thereof; (d) contacting the first plurality of blunt-ended fragments or fragments thereof with a second set of transposome complexes, individual transposome complexes of the second set comprising a second transposon sequence, to generate a second plurality of overhang fragments that comprise the second transposon sequence at a 5' end, wherein the first set of transposome complexes and the second set of transposome complexes are different in that: (i) transposon sequences comprised therein are distinct between the first and the second sets of transposome complexes; and/or (ii) one set of the transposome complexes utilized in step (a) or (d) are homodimer transposomes and one other set of the transposome complexes utilized are heterodimer transposomes; (e) subjecting the second plurality of overhang fragments to an additional extension reaction to generate a second plurality of blunt-ended fragments; and (f) generating sequence reads from the second plurality of blunt-ended fragments or derivatives thereof, thereby characterizing the double-stranded polynucleotide in the sample.

A first plurality of overhang fragments comprising the first transposon sequence at a 5' end can be formed by contacting the double-stranded polynucleotide with the first set of transposome complexes, through the process of transposition or tagmentation. Individual transposome complexes can comprise a transposase complexed with or bound to a first transposon sequence. The transposon sequence can comprise a transposon element, which can also be referred to as a transposase element. Transposases refer to enzymes capable of complexing with at least one transposon sequence and catalyzing insertion or transposition of the transposon sequence into a polynucleotide to yield a modified or "tagged" polynucleotide. Transposases, generally, can catalyze insertion or transposition of the transposon sequence to a polynucleotide by a cut and paste mechanism or a replicative transposition mechanism.

Transposases applicable for the subject methods can be of prokaryotic or eukaryotic origin. Example transposases include, but are not limited to, integrases, HERMES, and HIV integrases. Non-limiting examples of transposases which can be used in embodiments herein include Tn transposases (e.g. Tn3, Tn5, Tn7, Tn10, Tn552, Tn903), MuA transposases, Vibhar transposases (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, Tyl, any prokaryotic transposase, or any transposase related to and/or derived from those provided herein. In some embodiments, a subject method utilizes a Tn transposase, an MuA transposase, or a Vibhar transposase. In some cases, the transposase utilized in a subject method is a Tn transposase, for example, a Tn transposase selected from Tn3, Tn5, Tn7, and Tn10. In some cases, the transposomes comprise a dimer of monomers, individual monomers comprising a transposase and a transposon sequence. The transposome dimer can be a homodimer or a heterodimer. The transposon sequences of a homodimer may be the same transposon sequence. The transposon sequences of a heterodimer may be different transposon sequences. In some cases, the transposition reaction can be facilitated and/or triggered by addition of one or more cations. The cations can be divalent cations such as, for example, $Ca^{2+}$, $Mg^{2+}$ and $Mn^{2+}$.

A transposon sequence can comprise a nucleic acid, e.g., single- and/or double-stranded nucleic acid. A transposon sequence can be a double-stranded polynucleotide, for example completely double-stranded or partially double-stranded, e.g., having a single-stranded overhang, having a bubble, having a loop, etc. A transposon sequence generally includes a transposon element or a transposase element. A transposon element or transposase element can refer to a nucleic acid molecule, or portion thereof, that includes nucleotide sequences that form a transposome with a transposase or integrase enzyme. In some embodiments, a transposon element is capable of forming a functional complex (e.g., transposome) with a transposase in a transposition reaction. Non-limiting examples of transposon elements include the 19-bp outer end ("OE") transposon end, inner end ("IE") transposon end, or "mosaic end" ("ME") transposon end recognized by, for example, a wild-type or mutant Tn5 transposase, or the R1 and R2 transposon end recognized by MuA transposases. In some embodiments, the transposon element or transposase element of a transposon sequence used in embodiments herein is a ME transposon end. Transposon elements can comprise any nucleic acid or nucleic acid analogue suitable for forming a functional complex with the transposase or integrase. For example, the transposon element can comprise DNA, RNA, modified bases, non-natural bases, a modified backbone, or can comprise nicks in one or both strands.

During transposition or tagmentation, one strand of a double-stranded transposon sequence can be covalently linked to one strand of a double-stranded polynucleotide (e.g., the "transferred strand"). In some cases, the transferred strand is covalently linked to the 5' end of the one strand of the double-stranded polynucleotide. The other strand of the transposon sequence can be referred to as the "non-transferred strand." The non-transferred strand may not be linked to one strand of the double-stranded polynucleotide. In cases where a target polynucleotide for tagmentation is a double-stranded polynucleotide, the top strand of the double-stranded polynucleotide can be joined to a transposon sequence via tagmentation by a first transposase while the bottom strand of the same double-stranded polynucleotide can be joined at its 5' end to a another transposon sequence via tagmentation by a another transposase. The joining of a top strand of a double-stranded polynucleotide at its 5' end to a transposon sequence and the bottom strand of a double-stranded polynucleotide at its respective 5' end to a transposome sequence can yield an overhang fragment.

In some cases, the transposome breaks the double-stranded polynucleotide into fragments while covalently transferring the transposon sequence to the first strand of the polynucleotide fragment. In cases where the transposase catalyzes insertion or transposition of the transposon sequence to the target polynucleotide by a cut and paste mechanism, the target polynucleotide may be fragmented into shorter polynucleotides (e.g., fragments).

In some cases, the transposition reaction can include fragmentation prior to tagging of the polynucleotide with the transposon sequence. In some cases, fragmentation and tagging can occur simultaneously or substantially at the same time. In some cases, the transposase cleaves the polynucleotide to produce a staggered cut that generates overhangs. The overhangs can be 1 base pair (bp), 2 bp, 3 bp, 4 bp, 5 bp, 6 bp, 7 bp, 8 bp, 9 bp, 10 bp, or longer in length. For example, Tn5 can cleave the polynucleotide to produce 9 bp overhangs at 5' ends of the double stranded sequence. In some cases, the transposase cleaves the polynucleotide to produce a blunt end cut.

The transferred strand of a transposon sequence can remain hybridized to the non-transferred strand following tagmentation. In some embodiments, a gap between the non-transferred strand and one strand of the double-stranded target polynucleotide is formed. In some embodiments, the gap is filled by a polymerase and/or ligase. In some embodiments, the non-transferred strand of the transposon sequence does not remain hybridized to the transferred strand. In some embodiments, the non-transferred strand of the transposon sequence dissociates from the transferred strand, for example as a result of heat denaturation. In some embodiments, the non-transferred strand of the transposon sequence is displaced from the transferred strand, for example by action of strand displacing polymerase. In some embodiments, the non-transferred strand is separated from the transferred strand prior to an extension reaction. In some embodiments, this gap is not filled in by a polymerase and/or ligase.

Insertion of a transposon sequence by a transposase can be at a random or substantially random site in the double-stranded polynucleotide. The double-stranded polynucleotide can be of any of a variety of lengths. The size of the resulting overhang fragments can be any of a variety of lengths and may be dependent on the length of the starting polynucleotide. The size of the first plurality of overhang fragments can depend on, in some cases, the concentration of transposase during tagmentation.

In some embodiments, the double-stranded polynucleotide has a length of at least about 1 kilobase (kb), 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, 400 kb, 500 kb, 600 kb, 700 kb, 800 kb, 900 kb, 1 megabase (Mb), 2 Mb, 3 Mb, 4 Mb, 5 Mb, 6 Mb, 7 Mb, 8 Mb, 9 Mb, 10 Mb, 20 Mb, 30 Mb, 40 Mb, 50 Mb, 60 Mb, 70 Mb, 80 Mb, 90 Mb, 100 Mb, 200 Mb, 300 Mb, 400 Mb, 500 Mb, 600 Mb, 700 Mb, 800 Mb, or 900 Mb. In some embodiments, the double-stranded polynucleotide has a length of about 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 20 Mb, 30 Mb, 40 Mb, 50 Mb, 60 Mb, 70 Mb, 80 Mb, 90 Mb, 100 Mb, 200 Mb, 300 Mb, 400 Mb, 500 Mb, 600 Mb, 700 Mb, 800 Mb, or 900 Mb. In some embodiments, the double-stranded polynucleotide has a length of at most about 900 Mb, 800 Mb, 700 Mb, 600 Mb, 500 Mb, 400 Mb, 300 Mb, 200 Mb, 100 Mb, 90 Mb, 80 Mb, 70 Mb, 60 Mb, 50 Mb, 40 Mb, 30 Mb, 20 Mb, 10 Mb, 9 Mb, 8 Mb, 7 Mb, 6 Mb, 5 Mb, 4 Mb, 3 Mb, 2 Mb, 1 Mb, 900 kb, 800 kb, 700 kb, 600 kb, 500 kb, 400 kb, 300 kb, 200 kb, 100 kb, 90 kb, 80 kb, 70 kb, 60 kb, 50 kb, 40 kb, 30 kb, 20 kb, 10 kb, 9 kb, 8 kb, 7 kb, 6 kb, 5 kb, 4 kb, 3 kb, 2 kb, or 1 kb.

In some embodiments, the first plurality of overhang fragments comprises fragments having a length of at least about 50 bases, 75 bases, 100 bases, 125 bases, 150 bases, 175 bases, 200 bases, 225 bases, 250 bases, 275 bases, 300 bases, 325 bases, 350 bases, 375 bases, 400 bases, 425 bases, 450 bases, 475 bases, 500 bases, 525 bases, 550 bases, 575 bases, 600 bases, 625 bases, 650 bases, 675 bases, 700 bases, 725 bases, 750 bases, 775 bases, 800 bases, 825 bases, 850 bases, 875 bases, 900 bases, 925 bases, 950 bases, 975 bases, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, or 100 kb. In some embodiments, the first plurality of overhang fragments comprises fragments having a length of about 50 bases, 75 bases, 100 bases, 125 bases, 150 bases, 175 bases, 200 bases, 225 bases, 250 bases, 275 bases, 300 bases, 325 bases, 350 bases, 375 bases, 400 bases, 425 bases, 450 bases, 475 bases, 500 bases, 525 bases, 550 bases, 575 bases, 600 bases, 625 bases, 650 bases, 675 bases, 700 bases, 725 bases, 750 bases, 775 bases, 800 bases, 825 bases, 850 bases, 875 bases, 900 bases, 925 bases, 950 bases, 975 bases, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, or 100 kb. In some embodiments, the first plurality of overhang fragments comprises fragments having a length of at most about 100 kb, 90 kb, 80 kb, 70 kb, 60 kb, 50 kb, 40 kb, 30 kb, 20 kb, 10 kb, 9 kb, 8 kb, 7 kb, 6 kb, 5 kb, 4 kb, 3 kb, 2 kb, 1 kb, 975 bases, 950 bases, 925 bases, 900 bases, 875 bases, 850 bases, 825 bases, 800 bases, 775 bases, 750 bases, 725 bases, 700 bases, 675 bases, 650 bases, 625 bases, 600 bases, 575 bases, 550 bases, 525 bases, 500 bases, 475 bases, 450 bases, 425 bases, 400 bases, 375 bases, 350 bases, 325 bases, 300 bases, 275 bases, 250 bases, 225 bases, 200 bases, 175 bases, 150 bases, 125 bases, 100 bases, 75 bases, or 50 bases.

In some embodiments, a transposon sequence can include sequences in addition to a transposon element. In some embodiments, the additional sequences can be inserted into a target polynucleotide via the transposition reaction. The additional sequences can include a primer binding site, such as a sequencing primer site and/or an amplification primer site. Additional sequences can also include a cleavage site, an anchor site, a reporter tag, and a barcode. A primer binding site can include sequences for sequencing primers to anneal to a nucleic acid in a sequencing reaction or other extension reactions. Such additional sequences can be useful in downstream polynucleotide manipulation steps as well.

In some cases, following transposition, the transposase can be removed or inactivated before proceeding to the next step of a reaction. The transposase can be removed by any of a variety of suitable methods, including purification or inactivation, for example via denaturation or enzymatic treatment. Removal of the transposase can be useful in minimizing the inhibition to downstream reactions, such as extension reactions or amplification reactions that may use tagged fragments as templates. In some cases, a chemical treatment can be employed for removing the transposase. For example, the chemical treatment can include treating the tagged fragments with a detergent solution, such as an SDS solution. In some cases, the tagged fragments are not subjected to treatment to remove the transposase.

The first plurality of overhang fragments can be subjected to an extension reaction to generate a first plurality of blunt-ended fragments. The extension reaction can be used to fill in an overhang to yield a blunt-end. In the extension reaction, one strand of an overhang fragment may function as a primer while the other strand functions as the template. The extension reaction may involve use of a polymerase. The polymerase may be a strand-displacing polymerase capable of displacing the non-transferred strand.

Overhang fragments may have the first transposon sequence at a 5' end of a top strand and the first transposon sequence at a 5' end of the bottom strand. After extension to fill the overhang(s), individual top strands and bottom strands may comprise the first transposon sequence at a 5' end and a reverse complement of the first transposon sequence at a 3' end. As a result of sequence complementarity, the 5' end of an individual top strand or bottom strand can base pair with its own 3' end, thereby forming a stem loop or hair pin structure.

A primer-directed extension reaction can be conducted to generate copies of the first plurality of blunt-ended fragments or fragments thereof. Primer extension can be conducted with a primer comprising the first transposon sequence or a portion thereof. The primers can have a segment at a 5' end and a segment at a 3' end. In some cases, the primers can have additional segments interposed between the 5' and 3' ends or flanking the 5' and/or 3' ends. The segment at the 3' end can exhibit sequence complementarity to a blunt-ended fragment. The segment at the 5' end may also exhibit sequence complementarity to the blunt-ended fragment. The segment at the 3' end can exhibit sequence complementarity to the transposon sequence or a fragment thereof. The segment at the 5' end may also exhibit sequence complementarity to the transposon sequence or a fragment thereof. The segment at the 3' end may not exhibit sequence complementarity to the transposon sequence but rather a sequence of the polynucleotide. The segment at the 5' end also may not exhibit sequence complementarity to the transposon sequence but rather a sequence of the polynucleotide. The segment at the 5' end may not exhibit sequence complementarity to any portion of a blunt-ended fragment and may comprise an additional sequence that is appended to the sequence of the blunt-ended fragment when the copies are generated In some cases, the primer comprises the first transposon sequence or a portion thereof. Use of a primer comprising the first transposon sequence or a portion thereof may allow for the generation of copies of any blunt-ended fragment comprising the first transposon sequence. In some cases, copies of every blunt-ended fragment are generated. In some cases, copies of most blunt-ended fragments are generated. In some cases, copies of a majority of blunt-ended fragments are generated. In some embodiments, copies of at least 50%, 55%, 60%, 65%, 70%, 75%, 80%, 85%, 90%, or 95% of the blunt-ended fragments are generated during primer-directed extension. In some cases, this process can be referred to as single-primer amplification. In some cases, copies of the blunt-ended fragments are generated irrespective of the polynucleotide sequence between the transposon sequences. In some cases, use of a primer comprising the first transposon sequence can allow for unbiased amplification of the blunt-ended fragments.

In some cases, the segment at the 3' end of a primer may comprise gene-specific sequences. For example, where primer extension products comprising a particular gene sequence are desired for downstream analysis, the primer can comprise a segment at the 3' end capable of acting as a gene specific primer (e.g., having a gene-specific sequence). The gene-specific sequence of the primer can hybridize to a gene-specific tagged fragment and initiate primer extension. The extension reaction can select for, and in some cases, enrich a target sequence from a plurality of blunt-ended fragments. In some cases, primers having gene specific sequences corresponding to multiple genes can be used in combination to select for, and in some cases enrich, a plurality of gene specific blunt-ended fragments. For example, to generate extension products of tagged fragments corresponding to two gene sequences (e.g., gene 1 and gene 2), half of the primers may have a 3' segment with a sequence specific for gene 1 and half of the primers may have a 3' segment with a sequence specific for gene 2. For further example, to generate extension products of tagged fragments corresponding to three gene sequences (e.g., gene 1, gene 2, and gene 3), one-third of the primers may have a 3' segment with a sequence specific for gene 1, one-third of the primers may have a 3' segment with a sequence specific for gene 2, and one-third of the primers may have a 3' segment with a sequence specific for gene 3. The ratios of primers in a mixture can be optimized and/or adjusted as desired.

In some cases, the gene specific sequence can include a sequence targeting a cancer specific gene or a sequence implicated in cancer. In some cases, multiple primers, each being specific for one target gene, are utilized. In some cases, the primers of a subject method comprise a mixture of gene-specific primers and the mixture is used, for example, for multiplex processing. In some cases, the mixture of gene-specific primers target at least 5 genes (e.g., at least 10 genes, 15 genes, 20 genes, 25 genes, 50 genes, 100 genes, 200 genes, 300 genes, 400 genes, 500 genes, 600 genes, 700 genes, 800 genes, 900 genes, or 1,000 genes).

In some embodiments, the segment at the 5' end of an extension primer may lack sequence complementarity to a tagged fragment. In some embodiments, the 5' end of an extension primer comprises sequences that may be utilized in downstream sample processing steps. For example, the segment at the 5' end of an extension primer can comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

The first plurality of blunt-ended fragments or fragments thereof can be contacted with a second set of transposome complexes to generate a second plurality of overhang fragments that can comprise a second transposon sequence at a 5' end. Individual transposome complexes of the second set can comprise the second transposon sequence. In some embodiments, the second set of transposome complexes is a mixture of homodimer transposome complexes and further comprises transposome complexes having the first transposon sequence. In some embodiments, the mixture further comprises transposome complexes having a third transposon sequence, a fourth transposon sequence, a fifth transposon sequence, etc, as desired. In some embodiments, the second set of transposome complexes comprises heterodimer transposome complexes, individual transposome complexes comprising the first transposon sequence and the second transposon sequence. By using a mixture of homodimer transposome complexes having different transposon sequences or heterodimer transposome complexes having at least two transposon sequences, individual overhang fragments of the resulting second plurality of overhang fragments can have either a first transposon sequence, second transposon sequence, third transposon sequence, fourth transposon sequence, etc, at the 5' end. The second plurality of overhang fragments can comprise a plurality of fragments having different transposon ends. In some embodiments, the second set of transposome complexes comprises homodimer transposome complexes having a transposon sequence different from the first transposon sequence.

The size of the resulting overhang fragments can be of any of a variety of lengths and may be dependent on the length of the first plurality of blunt-ended fragments. The size of the second plurality of overhang fragments can depend on, in some cases, the concentration of transposase during tagmentation.

In some embodiments, the second plurality of overhang fragments comprises fragments having a length of at least about 10 bases, 20 bases, 30 bases, 40 bases, 50 bases, 75 bases, 100 bases, 125 bases, 150 bases, 175 bases, 200 bases, 225 bases, 250 bases, 275 bases, 300 bases, 325 bases, 350 bases, 375 bases, 400 bases, 425 bases, 450 bases, 475 bases, 500 bases, 525 bases, 550 bases, 575 bases, 600 bases, 625 bases, 650 bases, 675 bases, 700 bases, 725 bases, 750 bases, 775 bases, 800 bases, 825 bases, 850 bases, 875 bases, 900 bases, 925 bases, 950 bases, 975 bases, or 1 kb. In some embodiments, the first plurality of overhang fragments comprises fragments having a length of about 10 bases, 20 bases, 30 bases, 40 bases, 50 bases, 75 bases, 100 bases, 125 bases, 150 bases, 175 bases, 200 bases, 225 bases, 250 bases, 275 bases, 300 bases, 325 bases, 350 bases, 375 bases, 400 bases, 425 bases, 450 bases, 475 bases, 500 bases, 525 bases, 550 bases, 575 bases, 600 bases, 625 bases, 650 bases, 675 bases, 700 bases, 725 bases, 750 bases, 775 bases, 800 bases, 825 bases, 850 bases, 875 bases, 900 bases, 925 bases, 950 bases, 975 bases, or 1 kb. In some embodiments, the first plurality of overhang fragments comprises fragments having a length of at most about 1 kb, 975 bases, 950 bases, 925 bases, 900 bases, 875 bases, 850 bases, 825 bases, 800 bases, 775 bases, 750 bases, 725 bases, 700 bases, 675 bases, 650 bases, 625 bases, 600 bases, 575 bases, 550 bases, 525 bases, 500 bases, 475 bases, 450 bases, 425 bases, 400 bases, 375 bases, 350 bases, 325 bases, 300 bases, 275 bases, 250 bases, 225 bases, 200 bases, 175 bases, 150 bases, 125 bases, 100 bases, 75 bases, 50 bases, 40 bases, 30 bases, 20 bases, or 10 bases.

The second plurality of overhang fragments can be subjected to an additional extension reaction to generate a second plurality of blunt-ended fragments. The additional extension reaction can be useful in filling in an overhang to yield a blunt-end. In the additional extension reaction, one strand of an overhang fragment may function as a primer while the other strand functions as a template. The extension reaction may involve use of a polymerase. The polymerase may be a strand-displacing polymerase capable of displacing a non-transferred strand.

The second plurality of blunt-ended fragments or derivatives thereof can be sequenced to generate sequence reads, thereby characterizing the double-stranded polynucleotide in the sample. In some embodiments, the second plurality of blunt-ended fragments is subject to further nucleic acid processing in preparation for sequencing analysis. In some embodiments, sequencing primer binding sequences (e.g., Read1 or Read2), unique molecular identifiers or barcode sequences (e.g., i5, i7) and/or flow cell binding sequences (e.g., P5, P7) are attached or appended to the 5' and/or 3' ends of the fragments, for example by ligation, amplification, or a combination thereof.

An example is illustrated in FIG. 1. As shown in FIG. 1, a homodimer transposome comprising a first transposon sequence, X1-ME, can be used in a first transposition or tagmentation reaction to yield a first overhang fragment. The transferred strand of the double-stranded transposon sequence is covalently linked to one strand (e.g., top strand) of a double-stranded target polynucleotide, e.g., at a 5' end of the one strand, whereas the non-transferred strand of the transposon is not linked to the target polynucleotide. A transferred strand may also be linked to the other strand (e.g., bottom strand) of the double-stranded target polynucleotide, e.g., at a 5' end of the polynucleotide. The first overhang fragment can be subjected to an extension reaction to generate a first blunt-ended fragment. Following extension to fill the overhang, individual strands of the blunt-ended fragment can comprise the first transposon sequence (e.g., X1-ME) at a 5' end and a reverse complement of the first transposon sequence (e.g., X1'-ME') at the 3' end (e.g., copied during extension). In some cases, the first blunt-ended fragment forms a stem loop or hair pin structure as a result of sequence complementarity from the transposon sequences at the 5' and 3' ends. Next, a primer-directed extension reaction can be conducted with a primer comprising the first transposon sequence or a portion thereof to generate copies of the first plurality of blunt-ended fragments or fragments thereof. Use of a primer comprising the first transposon sequence or a portion thereof may allow for the generation of copies of any blunt-ended fragment comprising the first transposon sequence. Then, the first blunt-ended fragment or fragment thereof can be contacted with a second set of transposome complexes comprising a mixture of X1-ME homodimer transposome complexes and X2-ME homodimer transposome complexes to yield a second overhang fragment that comprises the second transposon sequence at a 5' end and/or the first transposon sequence at a 5' end. The second overhang fragment can comprise a reverse complement of the first transposon sequence at a 3' end. Some second overhang fragments may comprise the first transposon sequence at the 5' end and a reverse complement of the second transposon sequence at the 3' end. In some embodiments, X1 and X2 are not the same sequence.

Figure 2A:
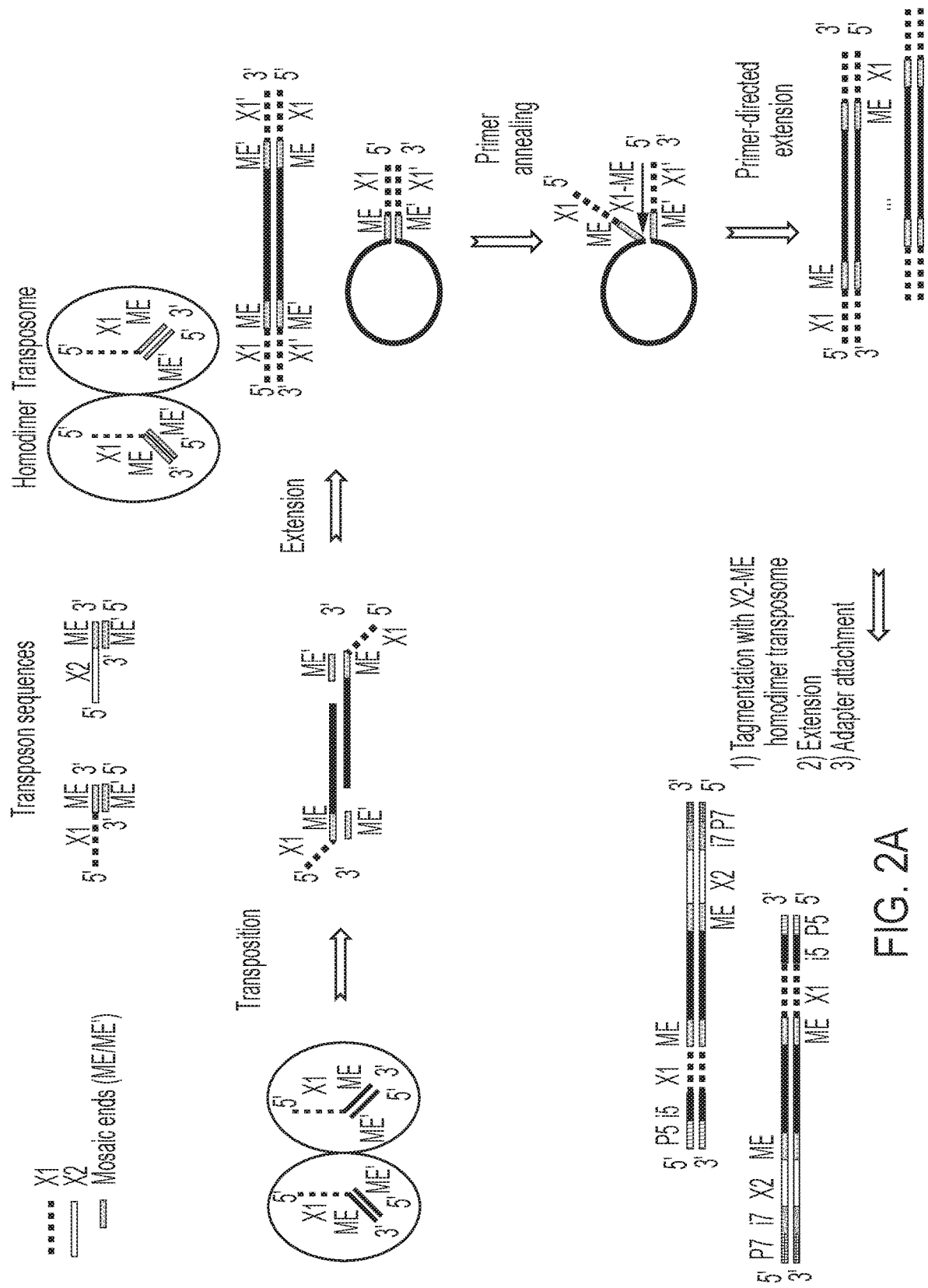
FIG. 2A illustrates a nonlimiting example method of characterizing a polynucleotide.

In some embodiments, the first set of transposome complexes and the second set of transposome complexes are different in that (i) transposon sequences comprised therein are distinct between the first and the second sets of transposon complexes. In some cases, the first set of transposome complexes and the second set of transposome complexes comprise homodimer transposome complexes. An example is illustrated in FIG. 2A. As shown in FIG. 2A, a homodimer transposome comprising a first transposon sequence, X1-ME, can be used in a first transposition or tagmentation reaction to yield a first overhang fragment. The transferred strand of the double-stranded transposon sequence is covalently linked to one strand (e.g., top strand) of a double-stranded target polynucleotide, e.g., at a 5' end of the one strand, whereas the non-transferred strand of the transposon is not linked to the target polynucleotide. A transferred strand may also be linked to the other strand (e.g., bottom strand) of the double-stranded target polynucleotide, e.g., at a 5' end of the polynucleotide. The first overhang fragment can be subjected to an extension reaction to generate a first blunt-ended fragment. Following extension to fill the overhang, individual strands of the blunt-ended fragment can comprise the first transposon sequence (e.g., X1-ME) at a 5' end and a reverse complement of the first transposon sequence (e.g., X1'-ME') at the 3' end (e.g., copied during extension). In some cases, the first blunt-ended fragment forms a stem loop or hair pin structure as a result of sequence complementarity from the transposon sequences at the 5' and 3' ends. Next, a primer-directed extension reaction can be conducted with a primer comprising the first transposon sequence or a portion thereof to generate copies of the first plurality of blunt-ended fragments or fragments thereof. Use of a primer comprising the first transposon sequence or a portion thereof may allow for the generation of copies of any blunt-ended fragment comprising the first transposon sequence. Then, the first blunt-ended fragment or fragment thereof can be contacted with a second set of homodimer transposomes comprising a second transposon sequence, X2-ME, to yield a second overhang fragment that comprises the second transposon sequence at the 5' end. The second overhang fragment can comprise a reverse complement of the first transposon sequence at a 3' end. Some second overhang fragments may comprise the first transposon sequence at the 5' end and a reverse complement of the second transposon sequence at the 3' end. In some embodiments, X1 and X2 are not the same sequence.

Figure 2B:
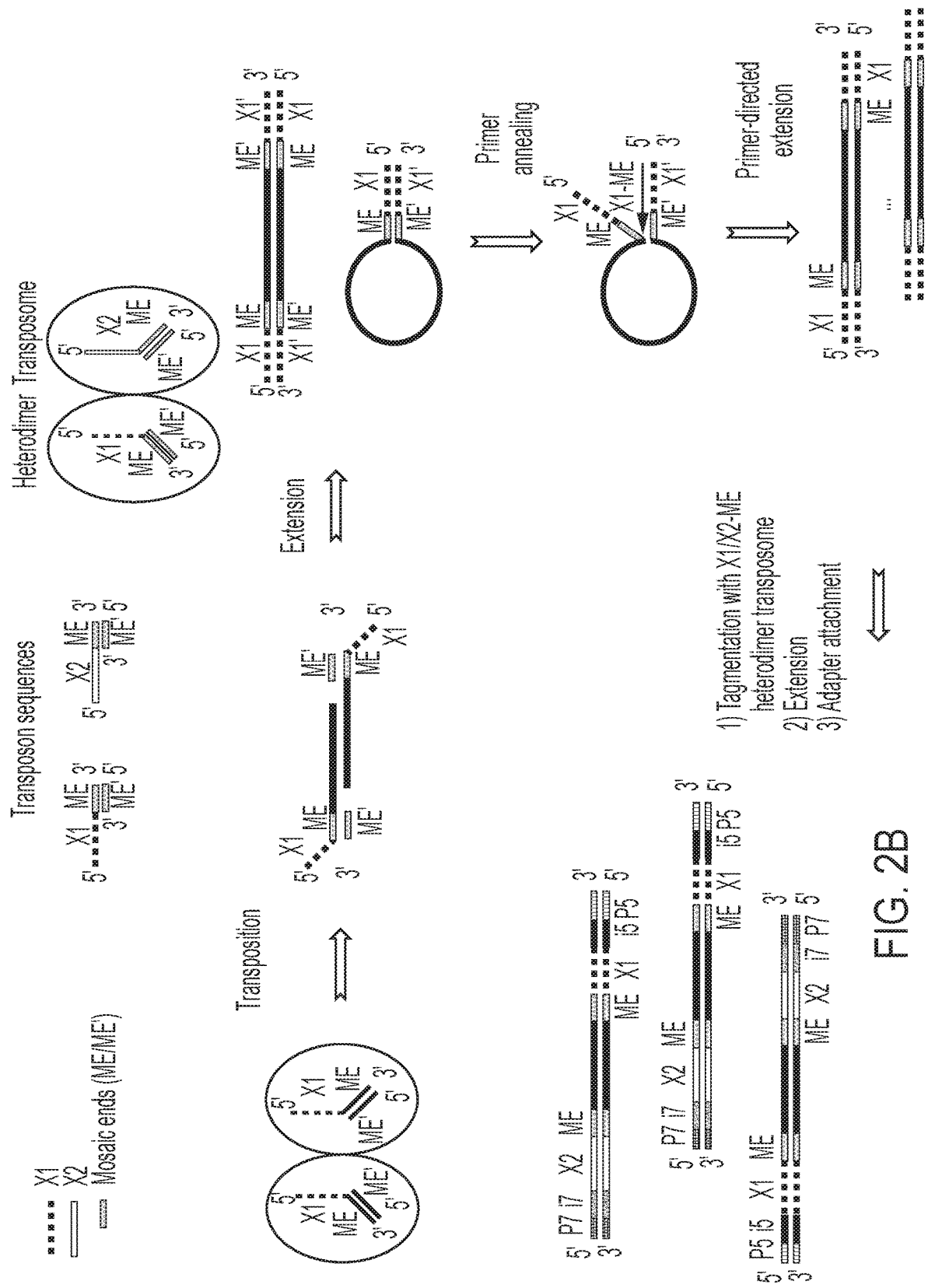
FIG. 2B illustrates a nonlimiting example method of characterizing a polynucleotide.

In some embodiments, the first set of transposome complexes comprises homodimer transposomes and the second set of transposome complexes comprises heterodimer transposomes. An example is illustrated in FIG. 2B. As shown in FIG. 2B, a homodimer transposome comprising a first transposon sequence, X1-ME, can be used in a first transposition or tagmentation reaction to yield a first overhang fragment. The transferred strand of the double-stranded transposon sequence is covalently linked to one strand (e.g., top strand) of a double-stranded target polynucleotide, e.g., at a 5' end of the one strand, whereas the non-transferred strand of the transposon is not linked to the target polynucleotide. A transferred strand may also be linked to the other strand (e.g., bottom strand) of the double-stranded target polynucleotide, e.g., at a 5' end of the polynucleotide. The first overhang fragment can be subjected to an extension reaction to generate a first blunt-ended fragment. Following extension to fill the overhang, individual strands of the blunt-ended fragment can comprise the first transposon sequence (e.g., X1-ME) at a 5' end and a reverse complement of the first transposon sequence (e.g., X1'-ME') at the 3' end (e.g., copied during extension). In some cases, the first blunt-ended fragment forms a stem loop or hair pin structure as a result of sequence complementarity from the transposon sequences at the 5' and 3' ends. Next, a primer-directed extension reaction can be conducted with a primer comprising the first transposon sequence or a portion thereof to generate copies of the first plurality of blunt-ended fragments or fragments thereof. Use of a primer comprising the first transposon sequence or a portion thereof may allow for the generation of copies of any blunt-ended fragment comprising the first transposon sequence. Then, the first blunt-ended fragment or fragment thereof can be contacted with a second set of transposomes comprising heterodimer transposomes to yield a second overhang fragment that comprises the second transposon sequence (e.g., X2-ME) at a 5' end. Individual complexes of the heterodimer transposomes can comprise X1-ME and X2-ME transposome sequences. The second overhang fragment can comprise a reverse complement of the first transposon sequence (e.g., X1'-ME') at a 3' end. Some second overhang fragments may comprise the first transposon sequence (e.g., X1-ME) at the 5' end and a reverse complement of the second transposon sequence (e.g., X2'-ME') at the 3' end. In some embodiments, X1 and X2 are not the same sequence.

Figure 3:
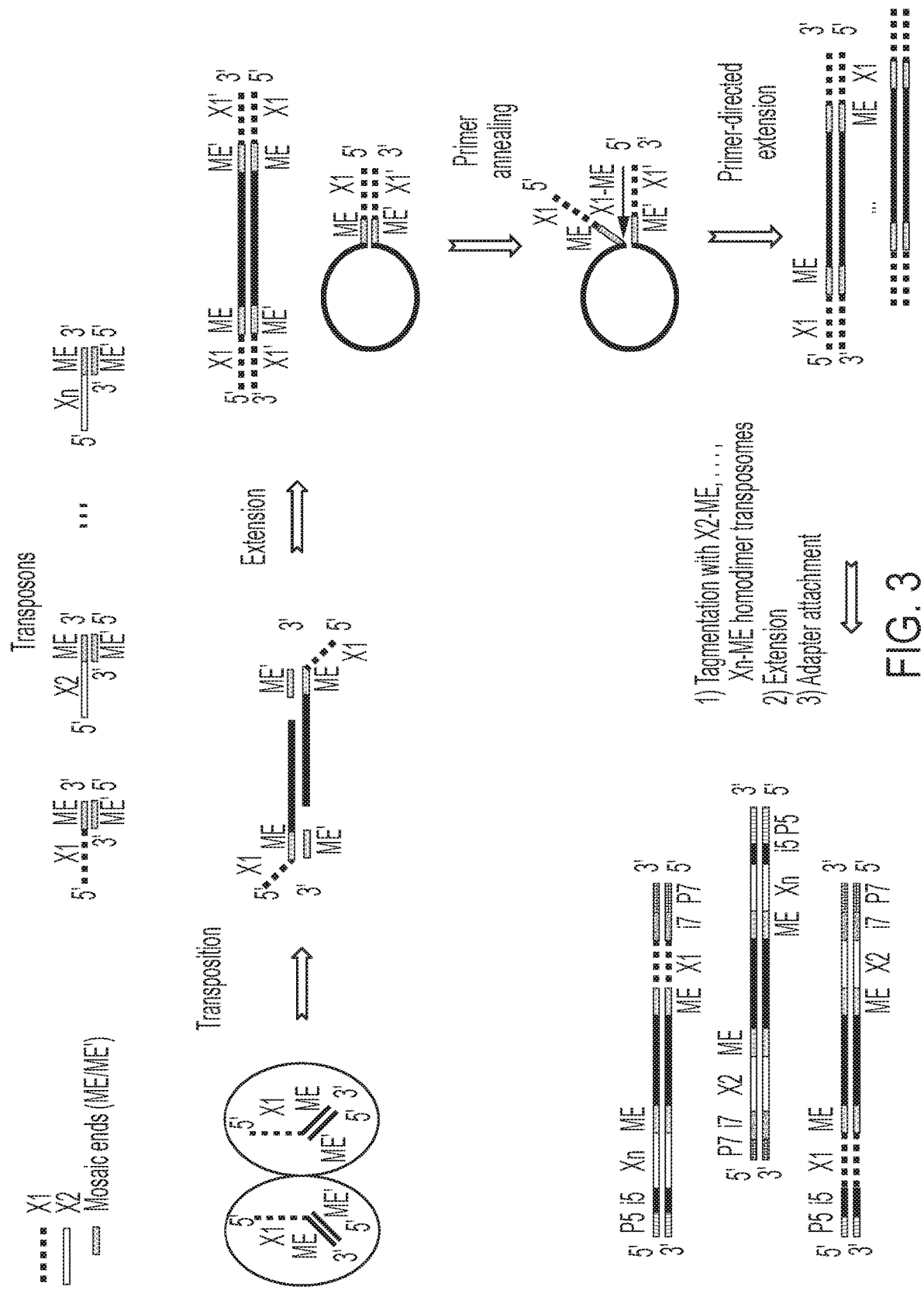
FIG. 3 illustrates a nonlimiting example method of characterizing a polynucleotide.

In some embodiments, in step (d), the second set of transposome complexes further comprises transposome complexes having at least a third transposon sequence. An example is illustrated in FIG. 3. As shown in FIG. 3, a homodimer transposome comprising a first transposon sequence, X1-ME, can be used in a first transposition or tagmentation reaction to yield a first overhang fragment. The transferred strand of the double-stranded transposon sequence is covalently linked to one strand (e.g., top strand) of a double-stranded target polynucleotide, e.g., at a 5' end of the one strand, whereas the non-transferred strand of the transposon is not linked to the target polynucleotide. A transferred strand may also be linked to the other strand (e.g., bottom strand) of the double-stranded target polynucleotide, e.g., at a 5' end of the polynucleotide. The first overhang fragment can be subjected to an extension reaction to generate a first blunt-ended fragment. Following extension to fill the overhang, individual strands of the blunt-ended fragment can comprise the first transposon sequence (e.g., X1-ME) at a 5' end and a reverse complement of the first transposon sequence (e.g., X1'-ME') at the 3' end (e.g., copied during extension). In some cases, the first blunt-ended fragment forms a stem loop or hair pin structure as a result of sequence complementarity from the transposon sequences at the 5' and 3' ends. Next, a primer-directed extension reaction can be conducted with a primer comprising the first transposon sequence or a portion thereof to generate copies of the first plurality of blunt-ended fragments or fragments thereof. Use of a primer comprising the first transposon sequence or a portion thereof may allow for the generation of copies of any blunt-ended fragment comprising the first transposon sequence. Then, the first blunt-ended fragment or fragment thereof can be contacted with at least two additional sets of transposome complexes, e.g., X2-ME transposomes, X3-ME transposomes, . . . , Xn-ME transposomes. The second overhang fragments can comprises the second transposon sequence at a 5' end (e.g., X2-ME, X3-ME, . . . , Xn-ME). The second overhang fragment can comprise a reverse complement of the first transposon sequence (e.g., X1'-ME') at a 3' end. Some second overhang fragments may comprise the first transposon sequence (e.g., X1-ME) at the 5' end and a reverse complement of the second transposon sequence at the 3' end.

In some embodiments, characterizing the double-stranded polynucleotide yields haplotype information. Haplotype information, in some cases, comprises haplotype phasing. In some embodiments, determining haplotype phasing comprises determining if a polynucleotide originated from a paternal chromosome or a maternal chromosome. Characterizing a double-stranded polynucleotide may comprise haplotype construction or genetic phasing. Methods disclosed herein can be used for building diploid reference genomes.

In some embodiments, the subject methods can be used to identify one or more sites of heterozygosity in a plurality of read pairs. Phasing data for allelic variants can be determined by identifying read pairs that comprise a pair of heterozygous sites. In some embodiments, the disclosure provides a method of haplotype phasing, comprising generating a plurality of read-pairs from a single DNA molecule and assembling a plurality of contigs of the DNA molecule using the read-pairs. In some embodiments, the haplotype phasing is performed at greater than 70%, 75%, 80%, 85%, 90%, or 95% accuracy. In some embodiments, the read-pairs span a distance greater than 0.5 kilo bases (kb), 1 kb, 2 kb, 3 kb, 4 kb, 5 kb, 10 kb, 15 kb, 20 kb, 30 kb, 40 kb, or 50 kb on the single DNA molecule. In some embodiments, at least 10%, 20%, 30%, 40%, 50%, 60%, 70%, 80%, or 90% of the read-pairs span a distance greater than 0.5 kilo bases (kb), 1 kb, 2 kb, 3 kb, 4 kb, 5 kb, 10 kb, 15 kb, 20 kb, 30 kb, 40 kb, or 50 kb on the single DNA molecule. In some embodiments, at least 1% of the read-pairs span a distance greater than 0.5 kilo bases (kb), 1 kb, 2 kb, 3 kb, 4 kb, 5 kb, 10 kb, 15 kb, 20 kb, 30 kb, 40 kb, or 50 kb on the single DNA molecule and the haplotvpe phasing is performed at greater than 70% accuracy.

In some embodiments, characterizing the double stranded-polynucleotide comprises identifying a structural variation in the polynucleotide. A structural variation can be, for example, a variation in the structure of a chromosome. A structural variation identified in a polynucleotide can include deletions, duplications, copy-number variants, insertions, inversions, and translocations. A structural variation can affect any length of the polynucleotide. The structural variation can be characterized by a loss of genetic material, a gain of genetic material, a translocation, a gene fusion and combinations thereof. In some cases, the structural variant is selected from the group consisting of insertion, deletion, duplication, transgene, translocation and gene fusion. Further examples of structural variants include copy number variants (CNV), short tandem repeats (STR), simple sequence repeats (SSR), variable number of tandem repeats (VNTR), amplified fragment length polymorphisms (AFLP), retrotransposon-based insertion polymorphisms, and sequence specific amplified polymorphism.

The present disclosure provides methods of identifying an allele, for example a low frequency allele. In an aspect, a method of identifying a low frequency allele comprises (a) contacting a double-stranded polynucleotide with transposome complexes, individual transposome complexes comprising a transposon sequence, to generate a plurality of overhang fragments that comprise the transposon sequence at a 5' end; (b) subjecting the plurality of overhang fragments to an extension reaction to generate a plurality of blunt-ended fragments; (c) conducting a first primer-directed extension reaction with a primer comprising the transposon sequence or a portion thereof and a first barcode sequence (X1) to generate a first plurality of barcoded polynucleotides comprising the first barcode sequence (X1) at a 5' end; (d) conducting a second primer-directed extension with a primer comprising the transposon sequence or a portion thereof and a second barcode sequence (X2) to generate a second plurality of barcoded polynucleotides comprising the second barcode sequence (X2) at a 5' end and a reverse complement of the first barcode sequence (X1') at a 3' end; (e) generating sequence reads from the second plurality of barcoded polynucleotides or derivatives thereof; and (f) identifying a low frequency allele in the double-stranded polynucleotide when the low frequency allele occurs in sequence reads of both a sense strand and an antisense strand of the double-stranded polynucleotide, wherein (i) sequence reads comprising, from 5' end to 3' end, (a) X2, the sense strand sequence, and X1' or (b) X1, the anti-sense strand sequence, and a reverse complement of X2 (X2'), are identified as originating from the sense strand of the double-stranded polynucleotide, and (ii) sequence reads comprising, from a 5' end to 3' end, (a) X1, the sense strand sequence, and X2' or (b) X2, the antisense strand sequence, and X1', are identified as originating from the antisense strand of the double-stranded polynucleotide.

Challenges to detecting an allele in a nucleic acid sample may include errors arising from sequencing, amplification, and other nucleic acid processing techniques. Such errors may be particularly challenging for alleles present in a nucleic acid sample at a low allele frequency. Alleles, for example, may be present in a nucleic acid sample at an allele frequency of less than about 50%, 45%, 40%, 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.1%, 0.01% or less. An allele present at a low frequency in a nucleic acid sample may be considered a "rare" allele.

In embodiments herein, a low frequency allele in a double-stranded polynucleotide which is present in a nucleic acid sample can be identified when the allele occurs in sequence reads of both a sense strand and an antisense strand of the double-stranded polynucleotide. The sequence reads originating from the sense strand and the antisense strand of the double-stranded polynucleotide can be identified by the combination of barcode sequences. Sequence reads comprising, from 5' end to 3' end, (a) X2, the sense strand sequence, and X1' or (b) X1, the antisense strand sequence, and X2', can be identified as originating from the sense strand of the double-stranded polynucleotide. Sequence reads comprising, from a 5' end to 3' end, (a) X1, the sense strand sequence, and X2' or (b) X2, the antisense strand sequence, and X1', can be identified as originating from the antisense strand of the double-stranded polynucleotide.

Figure 4:
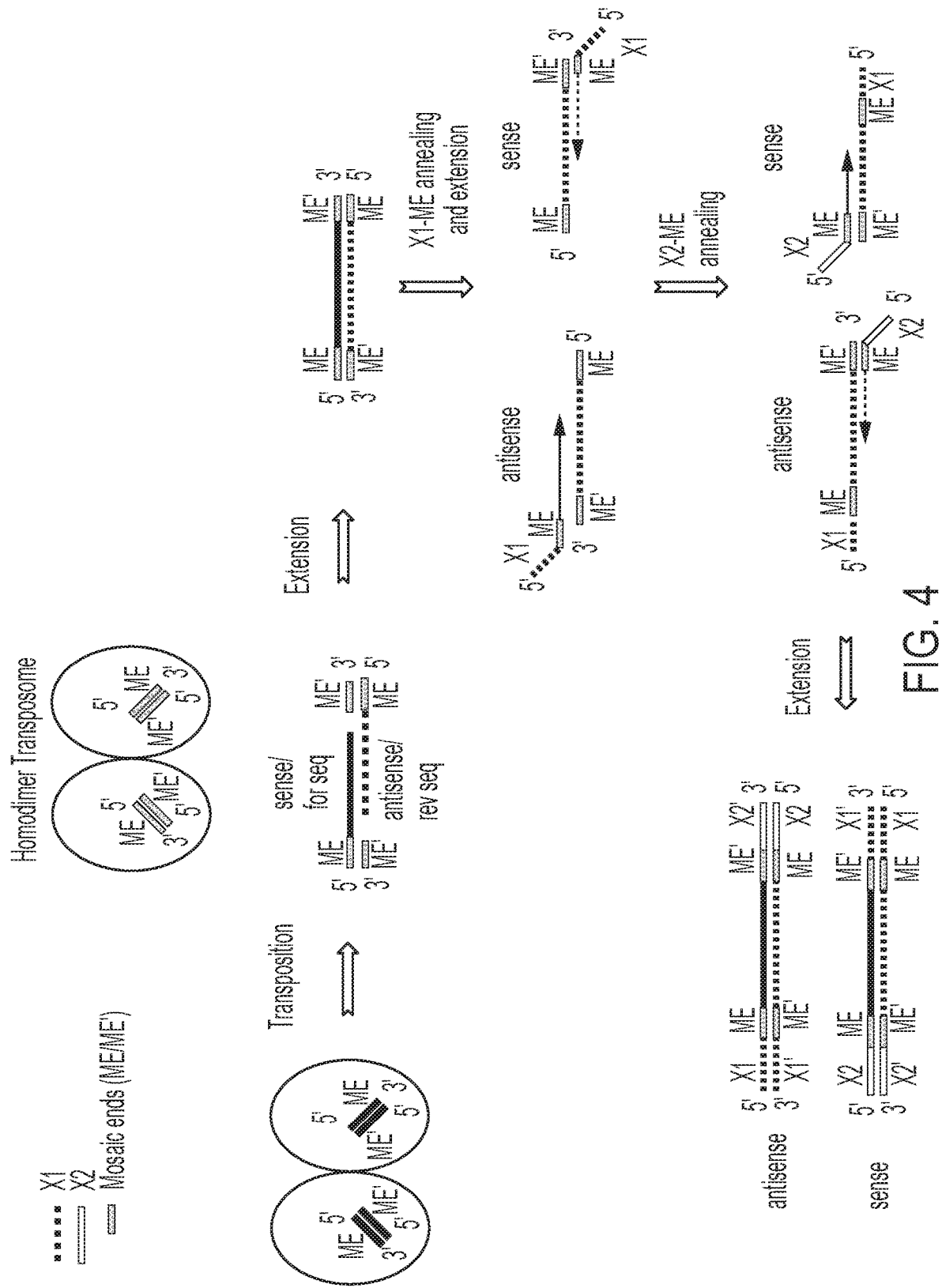
FIG. 4 illustrates a nonlimiting example method of identifying sense and antisense strands of a double-stranded polynucleotide.

FIG. 4 illustrates an example. As shown in FIG. 4, contacting a double-stranded polynucleotide with transposome complexes yields an overhang fragment that comprises the transposon sequence (e.g., ME) at a 5' end. In this example, the sense strand comprises the forward polynucleotide sequence (for seq) and the antisense strand comprises the reverse polynucleotide sequence (rev seq). Both the sense strand and antisense strand comprise the transposon sequence at respective 5' ends. The overhang fragment is subjected to an extension reaction to yield a blunt-ended fragment. The sense strand comprises the transposon sequence (e.g., ME) at the 5' end and a reverse complement of the transposon sequence (e.g., ME') at the 3' end. The antisense strand comprises ME at the 5' end and ME' at the 3' end. Next, a first plurality of barcoded polynucleotides comprising a first barcode sequence, X1, can be generated by conducting a primer-directed extension reaction with primers comprising the transposon sequence, ME, or a portion thereof and the first barcode sequence, X1. The transposon sequence, ME, of the primers can hybridize to ME' of the antisense strand and ME' of the sense strand to generate barcoded polynucleotides of both the sense and antisense strand via primer extension. Barcoded polynucleotides of the antisense strand can comprise, from 5' to 3' end, X1, ME, the forward sequence, and ME'. Copies of the sense strand can comprise, from 5' to 3' end, X1, ME, the reverse sequence, and ME'. Next, a second plurality of barcoded polynucleotides comprising a second barcode sequence, X2, can be generated by conducting a primer-directed extension reaction with primers comprising the transposon sequence, ME, or a portion thereof and the second barcode sequence, X2. The transposon sequence, ME, of the primer can hybridize to ME' of the first plurality of barcoded polynucleotides to generate the second plurality of barcoded polynucleotides. The transposon sequence, ME, of primers can hybridize to ME' of X1-barcoded polynucleotides of the antisense strand and ME' of X1-barcoded polynucleotides of the sense strand to yield X1/X2 barcoded polynucleotides of both the sense and antisense strand via primer extension. The second plurality of barcoded polynucleotides can comprise the sequence barcode sequence, X2, at a 5' end and a reverse complement of the first barcode sequence, X1', at a 3' end. Barcoded polynucleotides of the antisense strand can comprise, from 5' to 3' end, (i) X1, ME, the forward sequence, ME', and X2' or (ii) X2, ME, the reverse sequence, ME', and X1'. Barcoded polynucleotides of the sense strand can comprise, from 5' to 3' end, (i) X2, ME, the forward sequence, ME', and X1' or (ii) X1, ME, the reverse sequence, ME', and X2'.

The subject methods can detect a low frequency allele with an accuracy of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In some embodiments, the low frequency allele is present in a nucleic acid sample at an allele frequency of less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.1%, 0.01% or less.

The present disclosure provides methods of identifying a sequence variant. In an aspect, a method of identifying a sequence variant comprises (a) contacting a double-stranded polynucleotide with transposome complexes, individual transposome complexes comprising a transposon sequence, to generate a plurality of overhang fragments that comprise the transposon sequence at a 5' end; (b) subjecting the plurality of overhang fragments to an extension reaction to generate a plurality of blunt-ended fragments; (c) conducting a first primer-directed extension reaction with a primer comprising the transposon sequence or a portion thereof and a first barcode sequence (X1) to generate a first plurality of barcoded polynucleotides comprising the first barcode sequence (X1) at a 5' end; (d) conducting a second primer-directed extension with a primer comprising the transposon sequence or a portion thereof and a second barcode sequence (X2) to generate a second plurality of barcoded polynucleotides comprising the second barcode sequence (X2) at a 5' end and a reverse complement of the first barcode sequence (X1') at a 3' end; (e) generating sequence reads from the second plurality of barcoded polynucleotides or derivatives thereof; and (f) identifying a sequence variant in the double-stranded polynucleotide compared to a reference sequence when the sequence variant occurs in sequence reads of both a sense strand and an antisense strand of the double-stranded polynucleotide, wherein (i) sequence reads comprising, from 5' end to 3' end, (a) X2, the sense strand sequence, and X1' or (b) X1, the anti-sense strand sequence, and a reverse complement of X2 (X2'), are identified as originating from the sense strand of the double-stranded polynucleotide, and (ii) sequence reads comprising, from a 5' end to 3' end, (a) X1, the sense strand sequence, and X2' or (b) X2, the antisense strand sequence, and X1', are identified as originating from the antisense strand of the double-stranded polynucleotide.

Challenges to detecting a sequence variant in a nucleic acid sample may include errors arising from sequencing, amplification, and other nucleic acid processing techniques. Because sequence variants that are the result of amplification or sequencing errors are unlikely to be duplicated on both strands of a double-stranded polynucleotide (e.g. position and type), identifying a sequence variant in sequence reads of both a sense strand and antisense strand of a double-stranded polynucleotide can reduce the background of erroneous sequence variants.

The subject methods can be useful in detecting a sequence variant occurring at a frequency of about or less than about 50%, 45%, 40%, 35%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant is a rare sequence variant. In some cases, the sequence variant occurs at a frequency of about or less than about 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01%. The subject methods can detect a sequence variant (e.g., a rare sequence variant) with an accuracy of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The present disclosure provides methods of selectively sampling a subset of regions of a polynucleotide. In an aspect, a method of selectively sampling a subset of regions of a polynucleotide comprises (a) contacting a double-stranded polynucleotide with a first set of transposome complexes to generate a first plurality of overhang fragments that comprise a first transposon sequence or a second transposon sequence at a 5' end, wherein the first set of transposome complexes comprises a mixture of (i) homodimer transposases comprising the first transposon sequence, and (ii) homodimer transposases comprising the second transposon sequence; (b) subjecting the first plurality of overhang fragments to an extension reaction to generate a first plurality of blunt-ended fragments; (c) conducting a primer-directed extension reaction with a primer comprising the first transposon sequence or a portion thereof to selectively generate copies of a subset of the first plurality of blunt-ended fragments comprising the first transposon sequence or fragments thereof; (d) contacting the first plurality of blunt-ended fragments comprising the first transposon sequence or fragments thereof with a second set of transposome complexes to generate a second plurality of overhang fragments, wherein the second set of transposome complexes comprises (i) a plurality of homodimer transposases, or (ii) a plurality of heterodimer transposases; (e) subjecting the second plurality of overhang fragments to an additional extension reaction to generate a second plurality of blunt-ended fragments; and (f) generating sequence reads from the second plurality of blunt-ended fragments or derivatives thereof, thereby selectively sampling a subset of regions of the double-stranded polynucleotide. In some embodiments, the first set of transposome complexes comprises a mixture of (i) homodimer transposases comprising the first transposon sequence, (ii) homodimer transposases comprising the second transposon sequence, and (iii) heterodimer transposases comprising the first transposon sequence and the second transposon sequence.

Contacting a double-stranded polynucleotide with a first set of transposome complexes comprising a mixture of (i) homodimer transposases comprising the first transposon sequence (X1 homodimers), and (ii) homodimer transposases comprising the second transposon sequence (X2 homodimers), or (i) homodimer transposases comprising the first transposon sequence (X1 homodimers), (ii) homodimer transposases comprising the second transposon sequence (X2 homodimers), and (iii) heterodimer transposases comprising the first transposon sequence the second transposon sequence (X1/X2 heterodimers), can yield a first plurality of overhang fragments having different transposon ends. Some of the plurality of overhang fragments can comprise the first transposon sequence at 5' ends of both top and bottom strands (e.g., X1/X1). Some of the plurality of overhang fragments can comprise the first transposon at the 5' end of either the top or bottom strand, and the second transposon sequence at the 5' end of the other strand (e.g., X1/X2). Some of the plurality of overhang fragments can comprise the second transposon sequence at 5' ends of both top and bottom strands (e.g., X2/X2).

The relative ratio of X1/X1, X1/X2, and X2/X2 fragments can depend on the relative proportion of X1 homodimers, and X2 homodimers, and, optionally, X1/X2 heterodimers (if present). The relative ratio of X1/X1, X1/X2, and X2/X2 fragments can depend on the relative proportion of X1 and X2 transposon sequences in the mixture. In some cases, X1 homodimers and X2 homodimers are assembled separately, and then the homodimers are mixed together to yield a mixture. In some cases, X1 and X2 transposon sequences are mixed together and then assembled into transposome complexes such that the resulting mixture of transposome complexes comprises X1 homodimers, X2 homodimers, and X1/X2 heterodimers.

In some cases, the relative molar ratio of X1 and X2 transposons in the mixture is about 1:19, 2:18, 3:17, 4:16, 5:15, 6:14, 7:13, 8:12, 9:11, 10:10, 11:9, 12:8, 13:7, 14:6, 15:5, 16:4, 17:3, 18:2, or 19:1. In some cases, the relative molar ratio of X1 and X2 transposons in the mixture is about 1:9, 2:8, 3:7, 4:6, 5:5, 6:4, 7:3, 8:2, or 9:1. In some cases, the relative molar ratio of X1 and X2 transposons in the mixture is at least about 1:19, 2:18, 3:17, 4:16, 5:15, 6:14, 7:13, 8:12, 9:11, 10:10, 11:9, 12:8, 13:7, 14:6, 15:5, 16:4, 17:3, 18:2, or 19:1. In some cases, the relative molar ratio of X1 and X2 transposons in the mixture is at least about 1:9, 2:8, 3:7, 4:6, 5:5, 6:4, 7:3, 8:2, or 9:1.

The relative molar ratio of X1/X1, X1/X2, and X2/X2 fragments in the first plurality of overhang fragments may be about 1:81:18, or about 4:64:32, or about 9:49:42, or about 16:36:48, or about 25:25:50. In some embodiments, in the mixture of (i) homodimer transposases comprising the first transposon sequence, (ii) homodimer of transposases comprising the second transposon sequence, and (iii) heterodimer transposases comprising the first transposon sequence and the second transposon sequence, the molar concentration of (i) is less than that of (ii) and (iii). In some embodiments, in the mixture of (i) homodimer transposases comprising the first transposon sequence, (ii) homodimer of transposases comprising the second transposon sequence, and (iii) heterodimer transposases comprising the first transposon sequence and the second transposon sequence, the molar concentration of (ii) is less than that of (i) and (iii). In some embodiments, in the mixture of (i) homodimer transposases comprising the first transposon sequence, (ii) homodimer of transposases comprising the second transposon sequence, and (iii) heterodimer transposases comprising the first transposon sequence and the second transposon sequence, the molar concentration of (iii) is less than that of (i) and (ii). In some embodiments, in the mixture of (i) homodimer transposases comprising the first transposon sequence, and (ii) homodimer of transposases comprising the second transposon sequence, the molar concentration of (i) is less than that of (ii). In some embodiments, in the mixture of (i) homodimer transposases comprising the first transposon sequence, and (ii) homodimer of transposases comprising the second transposon sequence, the molar concentration of (ii) is less than that of (i).

While example ratios are provided herein, the subject methods are not limited to any particular ratio disclosed herein and can be adjusted to generate different ratios of X1/X1, X1/X2, and X2/X2 fragments.

Figure 5:
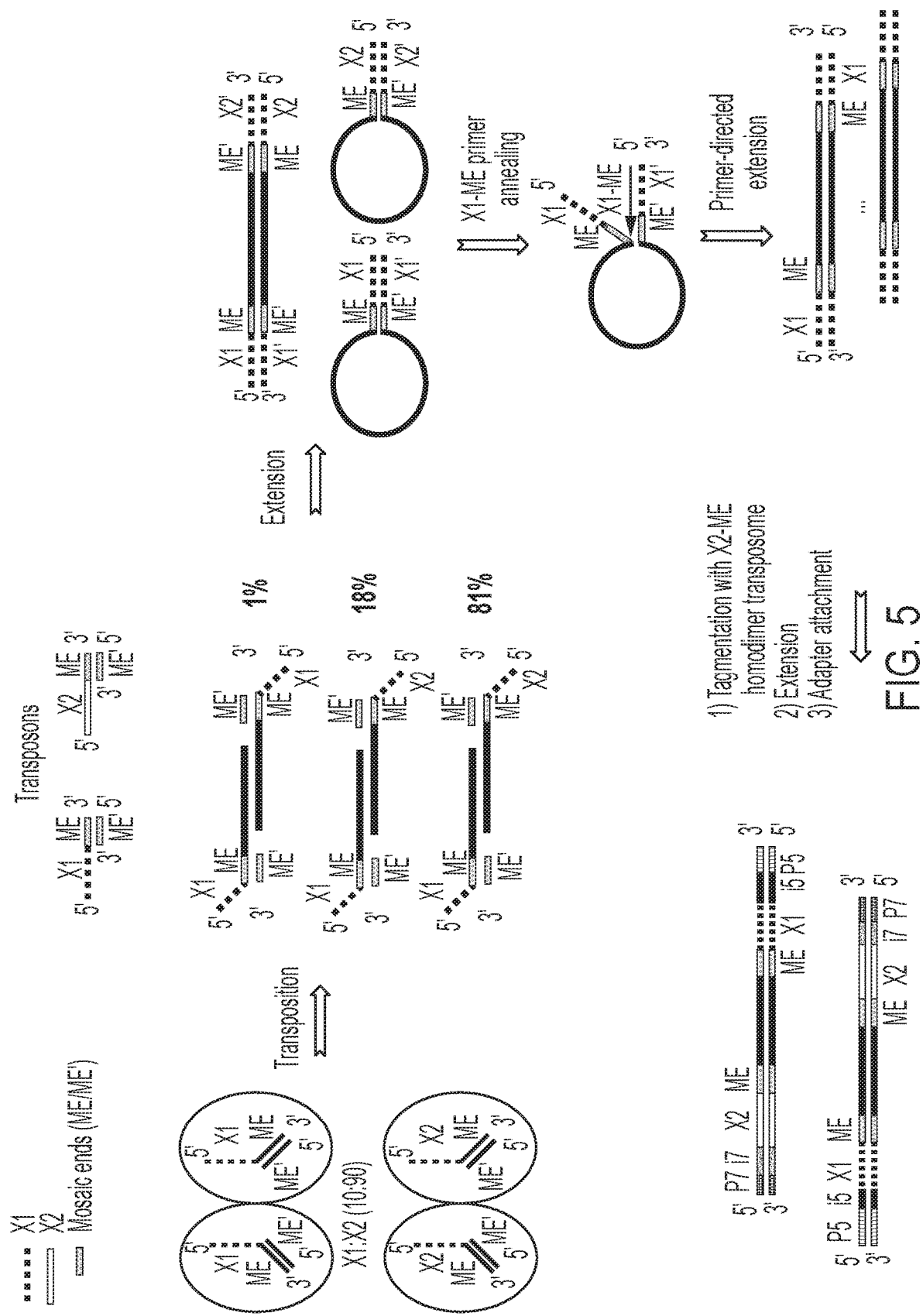
FIG. 5 illustrates a nonlimiting example method of selectively sampling a subset of regions of a polynucleotide.
Figure 6:
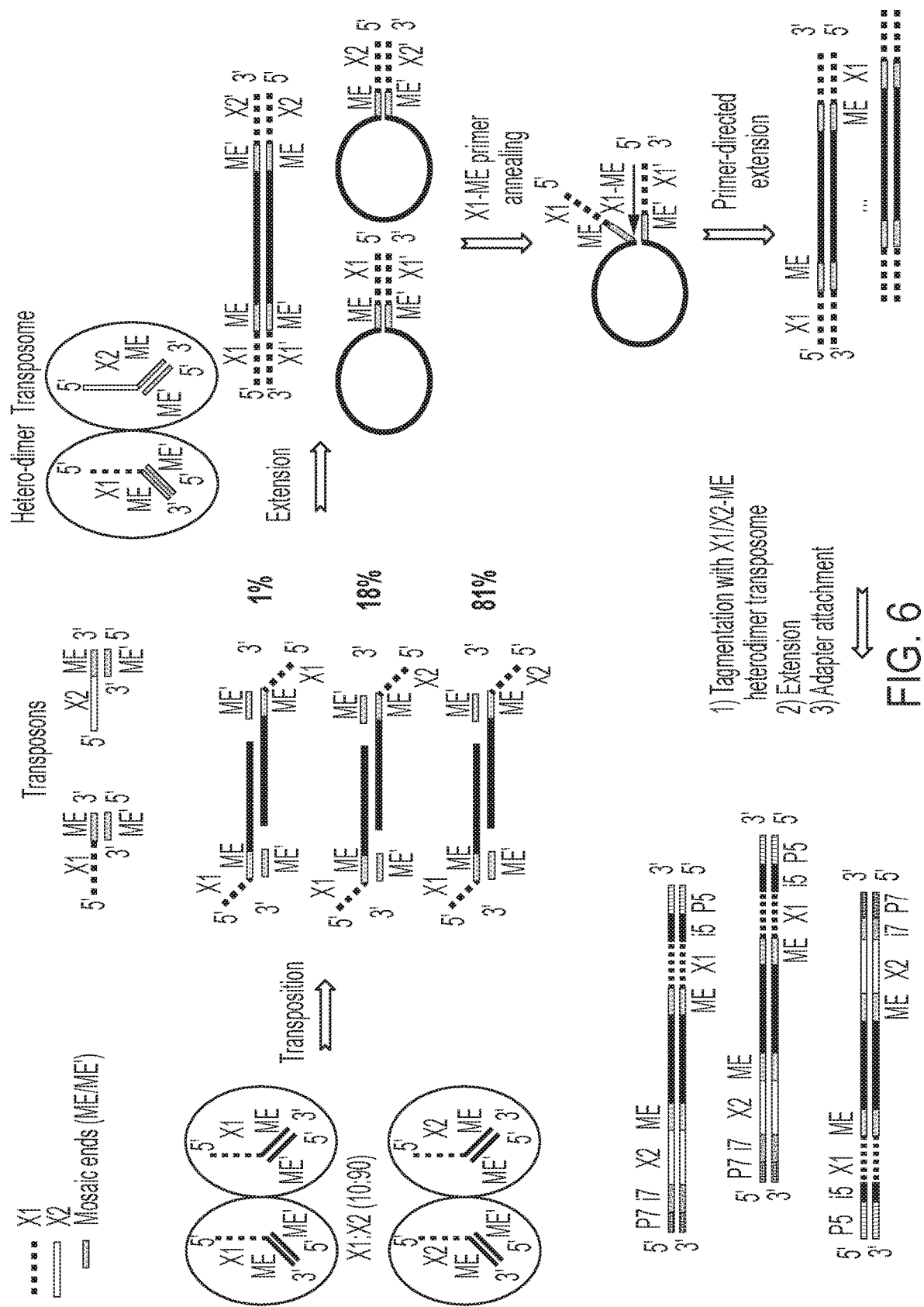
FIG. 6 illustrates a nonlimiting example method of selectively sampling a subset of regions of a polynucleotide.

FIGS. 5 and 6 illustrate examples. In this example, X1- and X2-containing transposons are present in the mixture at a ratio of about 10:90 (e.g., 1:9). Contacting a double-stranded polynucleotide with the transposome complexes generates a first plurality of overhang fragments that comprise X1 or X2 at the 5' end. The first plurality of overhang fragments may have different transposon ends. When using X1:X2 transposons at a ratio of about 1:9, about 1% of the first plurality of overhang fragments may comprise the first transposon sequence at 5' ends of both top and bottom strands (e.g., X1/X1), about 18% of the first plurality of overhang fragments may comprise the first transposon at the 5' end of either the top or bottom strand and the second transposon sequence at the 5' end of the other strand (e.g., X1/X2), and about 81% of the first plurality of overhang fragments may comprise the second transposon sequence at 5' ends of both top and bottom strands (e.g., X2/X2).

Next, the first plurality of overhang fragments can be subjected to an extension reaction to generate a first plurality of blunt-ended fragments. As shown in FIG. 5, single-stranded polynucleotides of the first plurality of blunt-ended fragments comprising X1 at a 5' end and a reverse complement of X1, e.g., X1', at a 3' end can form a stem-loop structure due to sequence complementarity. Similarly, single-stranded polynucleotides of the first plurality of blunt-ended fragments comprising X2 at a 5' end and a reverse complement of X2, e.g., X2', at a 3' end can also form a stem-loop structure due to sequence complementarity.

A primer-directed extension can be conducted with a primer comprising the first transposon sequence, X1, or a portion thereof, to selectively generate copies of a subset of the blunt-ended fragments comprising X1. Using a primer comprising the first transposon sequence, X1, or a portion thereof for primer-directed extension can allow for the selective sampling a subset of regions of the polynucleotide. In some cases, the linear polynucleotides (e.g., comprising X1 and X2 transposon sequences) can be removed from the stem-loop products prior to the extension reaction.

The blunt-ended fragments can then be contacted with a second set of transposome complexes to generate a second plurality of overhang fragments. The second set of transposome complexes may comprise a plurality of homodimer transposases, as shown in FIG. 5, or a plurality of heterodimer transposases, as shown in FIG. 6. Next, the second plurality of overhang fragments can be subjected to an additional extension reaction to yield a second plurality of blunt-ended fragments. The second plurality of blunt-ended fragments can be subjected to additional nucleic acid processing, such as adapter attachment and/or amplification by polymerase chain reaction (PCR). The second plurality of blunt-ended fragments, or derivatives thereof, can be sequenced to yield sequence reads, thereby selectively sampling a subset of regions of the double-stranded polynucleotide.

The present disclosure provides compositions for performing the subject methods. In some aspects, the present disclosure provides compositions resulting from performing any one or more of the steps of the subject methods.

In an aspect, the present disclosure provides a composition comprising a mixture of (i) homodimer transposases comprising a first transposon sequence, (ii) homodimer transposases comprising a second transposon sequence, and (iii) heterodimer transposases comprising the first transposon sequence and the second transposon sequence. In some cases, the relative ratio of X1 and X2 transposon sequences in the composition is about 1:19, 2:18, 3:17, 4:16, 5:15, 6:14, 7:13, 8:12, 9:11, 10:10, 11:9, 12:8, 13:7, 14:6, 15:5, 16:4, 13:7, 12:8, or 19:1. In some cases, the relative ratio of X1 and X2 transposon sequences in the composition is about 1:9, 2:8, 3:7, 4:6, 5:5, 6:4, 7:3, 8:2, or 9:1. In some cases, the relative ratio of X1 and X2 transposon sequences in the composition is at least about 1:19, 2:18, 3:17, 4:16, 5:15, 6:14, 7:13, 8:12, 9:11, 10:10, 11:9, 12:8, 13:7, 14:6, 15:5, 16:4, 13:7, 12:8, or 19:1. In some cases, the relative ratio of X1 and X2 transposon sequences in the composition is at least about 1:9, 2:8, 3:7, 4:6, 5:5, 6:4, 7:3, 8:2, or 9:1. In some embodiments, in the composition of (i) homodimer transposases comprising the first transposon sequence, (ii) homodimer of transposases comprising the second transposon sequence, and (iii) heterodimer transposases comprising the first transposon sequence and the second transposon sequence, the molar concentration of (i) is less than that of (ii) and (iii). In some embodiments, in the composition of (i) homodimer transposases comprising the first transposon sequence, (ii) homodimer of transposases comprising the second transposon sequence, and (iii) heterodimer transposases comprising the first transposon sequence and the second transposon sequence, the molar concentration of (ii) is less than that of (i) and (iii). In some embodiments, in the composition of (i) homodimer transposases comprising the first transposon sequence, (ii) homodimer of transposases comprising the second transposon sequence, and (iii) heterodimer transposases comprising the first transposon sequence and the second transposon sequence, the molar concentration of (iii) is less than that of (i) and (ii).

The present disclosure also provides reaction mixtures useful for performing any of the subject methods. A reaction mixture for performing a subject method can comprise one or more elements disclosed herein in relation to any of the various aspects or in any combination. In an aspect, the present disclosure provides a reaction mixture comprising a double-stranded polynucleotide and at least one transposome complex. In some embodiments, a reaction mixture can comprise an overhang fragment and at least one enzyme (e.g., a polymerase) for conducting an extension reaction. In some embodiments, a reaction mixture can comprise one or more primers for conducting primer-directed extension reaction. In some embodiments, a reaction mixture can comprise one or more barcoded primers for conducting primer-directed extension reaction.

In an aspect, the present disclosure provides a reaction mixture comprising (a) a mixture of (i) homodimer transposases comprising a first transposon sequence, (ii) homodimer transposases comprising a second transposon sequence, and optionally (iii) heterodimer transposases comprising the first transposon sequence and the second transposon sequence; and (b) a double-stranded polynucleotide. In some embodiments, the double-stranded polynucleotide comprises genomic DNA. The genomic DNA may comprise a single chromosome or fragment thereof. In some cases, the genomic DNA is from a single cell.

The present disclosure also provides kits useful for performing any of the subject methods. The kit can comprise one or more elements disclosed herein in relation to any of the various aspects or in any combination. A kit can comprise transposases, for example Tn transposases. A kit can comprise transposon sequences. A kit can comprise at least one enzyme for conducting an extension reaction. A kit can comprise at least one primer for conducting a primer-directed extension reaction. A kit can comprise at least one barcoded primer for conducting a primer-directed extension reaction.

In some embodiments, a kit can comprise (a) a first set of transposome complexes, individual transposome complexes of the first set comprising a first transposon sequence; (b) a primer comprising the first transposon sequence or a portion thereof; (c) a second set of transposome complexes, individual transposome complexes of the second set comprising a second transposon sequence; and (d) instructions for characterizing a polynucleotide sample, for example according to the subject methods. The first set of transposome complexes and the second set of transposome complexes can be different in that: (i) transposon sequences comprised therein are distinct between the first and the second sets of transposome complexes; and/or (ii) one set of the transposome complexes are homodimer transposomes and one other set of the transposome complexes are heterodimer transposomes.

In some embodiments, a kit can comprise (a) transposome complexes, individual transposome complexes comprising a transposon sequence; (b) a first primer comprising the transposon sequence or a portion thereof and first barcode sequence (X1); (c) a second primer comprising the transposon sequence or a portion thereof and a second barcode sequence (X2); and (d) instructions for identifying a low frequency allele or sequence variant in a polynucleotide, for example according to the subject methods.

In some embodiments, a kit can comprise (a) a first set of transposome complexes comprising: (i) homodimer transposases comprising a first transposon sequence, (ii) homodimer transposases comprising a second transposon sequence, and optionally (iii) heterodimer transposases comprising the first transposon sequence and the second transposon sequence; (b) a primer comprising the first transposon sequence or a portion thereof; (c) a second set of transposome complexes comprising (i) a plurality of homodimer transposases, or (ii) a plurality of heterodimer transposases; and (d) instructions for selectively sampling a subset of regions of a polynucleotide, for example according to the subject methods.

Contents of the kit may be contained in any suitable container. Each component may be packaged into different containers or where cross-reactivity and shelf-life permit, combinations of components can be provided in containers. Non-limiting examples of containers include a well, a plate, a tube, a chamber, a flow cell, or a chip.

The contents of the kit may be immediately usable for performing the methods described herein. In some cases, the contents of the kit are combined with other reagents in the kit or reagents supplied by a user prior to use in methods described herein. For example, a concentrated composition can be diluted prior to use or a lyophilized composition can be reconstituted prior to use.

A kit may provide buffers, non-limiting examples of which include sodium carbonate buffer, a sodium bicarbonate buffer, a borate buffer, a Tris buffer, a MOPS buffer, a HEPES buffer, and combinations thereof. A kit may comprise a control sample, e.g., purified DNA for use as a positive control or quantification standard.

In some embodiments, the kit further comprises adapter oligonucleotides. The adapter oligonucleotides can be single-stranded or double-stranded. The adapter may be attached to either a 5' end or a 3' end of a polynucleotide. In some cases, the adapter oligonucleotides comprise a barcode sequence, amplification primer binding sequence, sequencing primer binding sequence, or combinations thereof.

A transposase supplied in a kit can be any transposase described herein, including, but not limited to, integrase, HERMES, or HIV integrase. The transposase can be a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, Tyl, any prokaryotic transposase, or any transposase related to and/or derived from those listed above. In some embodiments, the transposase supplied in the kit is a Tn transposase, an MuA transposase, or a Vibhar transposase. In some cases, the transposase supplied in the kit is a Tn transposase selected from Tn3, Tn5, Tn7, and Tn10. In some cases, the transposomes comprise a dimer of monomers, individual monomers comprising a transposase and a transposon sequence. The transposome dimer can be a homodimer or a heterodimer. In some cases, the kit comprises one or more cations to facilitate and/or trigger a transposition reaction. The cations can be divalent cations such as, for example, $Ca^{2+}$, $Mg^{2+}$ and $Mn^{2+}$.

A transposon sequence supplied in a kit can be joined to a polynucleotide. A transposon sequence supplied in a kit can be a single-stranded, a double-stranded or a partially double-stranded polynucleotide sequence. In some cases, the transposon sequence can be either a double-stranded sequence or a partially double stranded sequence. A transposon sequence supplied in a kit can comprise any nucleic acid or nucleic acid analogue suitable for forming a functional complex with a transposase. The transposon sequence can comprise DNA, RNA, modified bases, non-natural bases, a modified backbone, or can comprise nicks in one or both strands.

A hot-start polymerase supplied in a kit can be used for an extension reaction and/or amplification reaction. Hot-start polymerases, such as high-fidelity PCR polymerases, can be activated by incubation at an elevated temperature for sufficient length of time (e.g., 95 degrees for 1 min).

In some cases, the kit can include an SDS solution for inactivating a transposase. For example, SDS solutions with 0.1%, 0.2% or more SDS can be included in the kit.

In an aspect, the present disclosure provides a system for performing methods disclosed herein. The system can comprise (a) a computer configured to receive a user request to characterize a polynucleotide, identify a low frequency allele, identify a sequence variant, or selectively sample a subset of regions of a polynucleotide; (b) one or more processors configured to execute commands that effect a tagmentation reaction and one or more extension reactions (including primer-directed extension reactions) on a polynucleotide or a portion thereof in response to the user request; and/or (c) a sequencing system capable of generating sequence reads. In some embodiments, the computer comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to design primers for amplifying a specified target sequence (which may also be provided by the customer). The computer may receive the customer request directly (e.g. by way of an input device such as a keyboard, mouse, or touch screen operated by the customer or a user entering a customer request) or indirectly (e.g. through a wired or wireless connection, including over the internet).

In some embodiments, the system comprises a report generator that sends a report to a recipient, wherein the report contains information about a polynucleotide in a sample. For example, the report may contain haplotype information or identification of a structural variation in a polynucleotide. The report may contain information about a low frequency allele or sequence variant. The report may contain information about a subset of regions of a polynucleotide that was selectively sampled. The report generator may send a report automatically in response to the customer request. Alternatively, the report generator may send a report in response to instructions from an operator. The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be but is not limited to the customer, or electronic system (e.g. one or more computers, and/or one or more servers). In some embodiments, the report generator sends the report to a recipient's device, such as a personal computer, phone, tablet, or other device. The report may be viewed online, saved on the recipient's device, or printed.

In an aspect, the disclosure provides a computer-readable medium comprising codes that, upon execution by one or more processors, implements a method according to any of the methods disclosed herein. Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the extension reaction and/or amplification reaction, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

In various embodiments of the aspects herein, a transposome comprises a transposase complexed with a transposon sequence. The transposase can be any naturally occurring transposase or an engineered (e.g., mutated or mutant transposase). Transposases, as previously described, refer to enzymes capable of complexing with at least one transposon sequence and catalyzing insertion or transposition of the transposon sequence into a target polynucleotide. Transposases can be of prokaryotic or eukaryotic origin.

Example transposases include, but are not limited to, integrases, HERMES, and HIV integrases. Non-limiting examples of transposases include Tn transposases (e.g. Tn3, Tn5, Tn7, Tn10, Tn552, Tn903), MuA transposases, Vibhar transposases (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, Tyl, or any transposase related to and/or derived from those disclosed herein. In various embodiments of the aspects herein, the transposase of a transposome is a Tn transposase, an MuA transposase, or a Vibhar transposase. In some cases, the transposase is a Tn transposase, for example, a transposase selected from Tn3, Tn5, Tn7, and Tn10. In some embodiments, the transposase is Tn5 or a variant thereof. In some cases, the transposomes comprise a dimer of monomers comprising a transposase and a transposon sequence. The transposome dimer can be a homodimer or a heterodimer. In some cases, the transposition reaction can be facilitated and/or triggered by addition of one or more cations. The cations can be divalent cations such as, for example, $Ca^{2+}$, $Mg^{2+}$ and $Mn^{2+}$.

In some cases, the transposase is an engineered transposase. The engineered transposase can have different properties relative to the parent transposase from which it was derived. In some cases, the transposase is a hyperactive transposase. In some cases, the engineered transposase can be capable of binding polynucleotides comprising modified nucleotides or nucleotide analogs. A transposase of the disclosure, for example, can be an engineered transposase which binds to any polynucleotide sequence in an unbiased manner. In some cases, a transposase of the disclosure is an engineered or mutant transposase comprising a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence identity to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. An engineered or mutant transposase of the disclosure may have increased transposition activity compared to the parent transposase. In some cases, the engineered or mutant transposase has at least about 5%, 10%, 15%, 20%, 25%, 30%, 35%, 40%, 45%, or 50% greater activity than the parent transposase. An engineered or mutant transposase of the disclosure may have decreased transposition activity compared to the parent transposase. In some cases, an engineered or mutant transposase has at least about 5%, 10%, 15%, 20%, 25%, 30%, 35%, 40%, 45%, or 50% lower activity than the parent transposase.

In various embodiments of the aspects herein, transposon sequences can be DNA, RNA or reverse transcribed RNA (e.g., cDNA). A transposon element of a transposon sequence can be recognized by transposases and can be referred to as a recognition sequence. Recognition sequences can include the entire transposon sequence or any portion thereof. In some cases, either both ends or a single end of the transposon sequence can be recognized by a transposase. For example, Tn5 transposase can recognize a 19 bp sequence on either end of the transposon sequence.

In some cases, a transposon sequence can join to a polynucleotide in a sequence-dependent manner. For example, transposons Passport, Himar1, Hsmar1, Frog Prince, and Sleeping Beauty may preferentially join to polynucleotide sequences enriched in 'TA'. Similarly, transposons PiggyBac and PiggyBat may preferentially join to the polynucleotide sequences enriched in 'TTAA'. In some cases, a transposon sequence can join to polynucleotide sequences in a sequence-independent manner, or substantially sequence-independent manner. For example, transposons Tol2 and TcBuster can join to any polynucleotide sequences that are 8 bp long. Transposons can be substantially methylated, partially methylated, hemimethylated or substantially unmethylated.

Any of a variety of polynucleotides can be characterized by methods of the present disclosure. In some embodiments, the polynucleotide characterized is a cell-free polynucleotide. In some embodiments, the cell-free polynucleotide is cell-free DNA (cfDNA) or cell-free RNA (cfRNA). For example, a cell-free polynucleotide can be circulating tumor DNA, circulating tumor RNA, circulating fetal DNA, or circulating fetal RNA. In some embodiments, the polynucleotide characterized can be a genomic polynucleotide. In some cases, the genomic polynucleotide can comprise genomic DNA, genomic RNA or a mixture of genomic DNA and genomic RNA. In some cases, the genomic polynucleotide can exhibit high integrity, such as high molecular weight polynucleotides. In some cases, the genomic polynucleotide can be further bound to proteins, such as histones. In some cases, the genomic polynucleotide can be fragmented. In some cases, the polynucleotide can be methylated, such as 5-methylcytosine (e.g., partially or completely). In some cases, the polynucleotide can be unmethylated. In some cases the genomic polynucleotide comprises a chromosome. A chromosome can be any chromosome of eukaryotic cell or a prokaryotic cell.

The polynucleotide can be from a polynucleotide sample. In some cases, the polynucleotides can be obtained from intact cells or tissues. The polynucleotide may be from a single cell. In some cases, the polynucleotides can be obtained from bodily fluids, such as blood, saliva, urine, amniotic fluid, plasma, mucous, cerebral spinal fluid, tears, synovial fluid, lymph, lactal duct fluid, and semen, etc. In certain embodiments, the polynucleotides are isolated from fresh tissues. In other cases, the polynucleotide sample can be isolated from frozen tissues. In yet other cases, the polynucleotide sample can be isolated from fixed tissues, such as formalin-fixed paraffin-embedded (FFPE) tissues. Further examples of sources of polynucleotide samples include, but are not limited to, cells dissociated from tissues, blood cells, bacteria, virus, mitochondria, chloroplast, in vitro assembled protein DNA complexes, and neutrophil extracellular traps. In some cases, the polynucleotide can be obtained from a culture of cells, e.g., a cell line. The polynucleotide can be fragmented to yield fragments suitable for downstream assays.

Cell-free polynucleotides include polynucleotides originating from a cell but not directly obtained from a cellular source, such as a tissue sample. Non-limiting examples of sources from which cell-free polynucleotides may originate are normal cells and tissue, abnormal cells and tissue (e.g., diseased cells or tissue, e.g., cancerous cells or tissue), fetal cells and tissue, and pathogens. A cell-free polynucleotide present in a non-cellular source can result from cell death (e.g., apoptosis or necrosis) or cell shedding. Sequence analysis of cell-free polynucleotides can be used to characterize the cell or population of cells from which the cell-free polynucleotide is derived, such as tumor cells (e.g., in cancer detection), fetal cells (e.g., in prenatal diagnostics), cells from transplanted tissue (e.g., in early detection of transplant failure), or a pathogen (e.g., bacteria or virus).

Any polynucleotide can be used by embodiments of the present disclosure. Polynucleotides can be obtained from a subject, such as any animal or living organism. Non-limiting examples of subjects are mammals, such as humans, non-human primates, rodents such as mice and rats, dogs, cats, pigs, sheep, rabbits and others. In some embodiments, a subject is healthy, and polynucleotides obtained from the subject may not comprise a sequence variant associated with a disease or disorder. In some embodiments, a subject is suspected of having a disease or disorder, and polynucleotides obtained from the subject may comprise a sequence variant associated with the disease or disorder. In some embodiments, a subject is pregnant, and polynucleotides obtained from the subject comprise fetal polynucleotides.

Cell-free polynucleotides can be obtained from various non-cellular sources. Non-limiting examples of non-cellular sources from which cell-free polynucleotides can be obtained are serum, plasma, blood, perspiration, saliva, urine, stool, semen, mucosal excretions, spinal fluid, amniotic fluid, and lymph fluid. Various methods for collecting samples of non-cellular sources from which cell-free polynucleotides can be obtained are available. In some embodiments, samples of non-cellular sources from which cell-free polynucleotides can be obtained are from a subject. In some embodiments, samples are obtained by venipuncture. In some embodiments, samples are obtained by aspiration.

Various methods and commercial kits are available for obtaining cell-free polynucleotides, such as cell-free DNA or RNA, from a sample. Examples of methods and kits for extracting and isolating cell-free polynucleotides, including cell-free DNA, are phenol/chloroform extraction, phenol/chloroform/isoamyl alcohol (PCI)-glycogen extraction, NaI (sodium iodide) extraction, guanidine-resin extraction, the QIAmp DNA Blood Midi kit with carrier RNA, the ChargeSwitch serum kit, the ZR serum DNA kit, Qiagen Qubit™ dsDNA HS Assay kit, Agilent™ DNA 1000 kit, TruSeq™ Sequencing Library Preparation, and the Puregene DNA purification system Blood Kit.

Cell-free polynucleotides, including cell-free DNA and RNA, can be extracted and isolated from bodily fluids through a partitioning step in which cell-free polynucleotides are separated from cells and other non-soluble components of the bodily fluid. Examples of partitioning techniques are centrifugation and filtration. In some embodiments, cells are not partitioned from cell-free polynucleotides first, but rather lysed. In some embodiments, the genomic DNA of intact cells is partitioned through selective precipitation. Cell-free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments of any of the various aspects disclosed herein, a polynucleotide or a target polynucleotide comprises genomic DNA. In some embodiments, a polynucleotide or a target polynucleotide is derived from genomic DNA. Genomic DNA can be obtained from a cell or tissue sample using various methods and commercial kits available, such as a Qiagen DNeasy Tissue Kit. Genomic DNA can be obtained and purified from a sample using any extraction, isolation, and purification method previously described elsewhere herein. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). For example, nucleic acids can be isolated and purified using solid phase reversible immobilization (SPRI) beads (Agencourt AMPure XP). In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodide, Hoechst stain, SYBR gold, ethidium bromide).

In some embodiments, a polynucleotide or a target polynucleotide comprises fragmented cell-free DNA or fragmented genomic DNA. In some cases, fragmenting occurs as a result or prior sample processing steps, such as formalin fixation, paraffin embedding, or freezing. In some cases, a polynucleotide is fragmented to yield shorter fragments.

Various methods are available for fragmenting polynucleotides, including but not limited to chemical, enzymatic, and mechanical methods such as sonication, shearing, and contacting with restriction enzymes. In some embodiments, cell-free DNA fragments are approximately uniform in length. In some embodiments, cell-free DNA fragments are not approximately uniform in length. In some embodiments, cell-free DNA fragments have an average length from about 50 to about 1000 nucleotides in length. In some embodiments, cell-free DNA fragments have an average length from about 50 to about 500 nucleotides in length. In some embodiments, cell-free DNA fragments have an average length from about 50 to about 250 nucleotides in length. In some embodiments, cell-free DNA fragments have an average length from about 50 to about 200 nucleotides in length. In some embodiments, cell-free DNA fragments have an average length from about 50 to about 100 nucleotides in length. In some embodiments, cell-free DNA fragments have an average length from about 40 to about 1000 nucleotides in length. In some embodiments, cell-free DNA fragments have an average length from about 40 to about 500 nucleotides in length. In some embodiments, cell-free DNA fragments have an average length from about 40 to about 250 nucleotides in length. In some embodiments, cell-free DNA fragments have an average length from about 40 to about 200 nucleotides in length. In some embodiments, cell-free DNA fragments have an average length from about 40 to about 100 nucleotides in length.

In some embodiments, genomic DNA is fragmented into polynucleotides of shorter lengths. In some embodiments, genomic DNA fragments are approximately uniform in length. In some embodiments, genomic DNA fragments are not approximately uniform in length. In some embodiments, genomic DNA fragments have an average length from about 50 to about 100 nucleotides in length. In some embodiments, genomic DNA fragments have an average length from about 50 and 250 nucleotides in length. In some embodiments, genomic DNA fragments have an average length from about 50 and 500 nucleotides in length. In some embodiments, genomic DNA fragments have an average length from about 50 and 750 nucleotides in length. In some embodiments, genomic DNA fragments have an average length from about 100 and 1000 nucleotides in length.

In some cases, the polynucleotides can be obtained from intact cells or tissues. In some cases, the polynucleotides can be obtained from bodily fluids, such as blood, saliva, urine, amniotic fluid, plasma, mucous, cerebral spinal fluid, tears, synovial fluid, lymph, lactal duct fluid, and semen, etc. In certain embodiments, the polynucleotides are isolated from fresh tissues. In other cases, the polynucleotide sample can be isolated from frozen tissues. In yet other cases, the polynucleotide sample can be isolated from fixed tissues. Further examples of sources of polynucleotide samples include, but are not limited to, cells dissociated from tissues, blood cells, cells obtained from formalin-fixed paraffin embedded (FFPE) tissues, bacteria, virus, mitochondria, chloroplast, in vitro assembled protein DNA complexes, and neutrophil extracellular traps. In some cases, the polynucleotide can be obtained from a culture of cells, e.g., a cell line.

Some embodiments of the present disclosure comprise primer extension and amplification reactions, such as generating extension products and amplifying extension products. Primer extension reactions can involve changes in temperature (thermocycling) or a constant temperature (isothermal). In some embodiments, primer extension reactions comprise polymerase chain reaction (PCR). PCR involves cycling through multiple stages of denaturation, annealing of primer pairs to opposite strands, and primer extension to exponentially increase copy numbers of the target sequence, at least some of these stages generally occurring at different reaction temperatures. Non-limiting examples of PCR amplification techniques are quantitative PCR (qPCR or realtime PCR), reverse transcription PCR (RT-PCR), digital PCR (dPCR or dePCR), target-specific PCR, and quantitative reverse transcription PCR (qRT-PCR). Examples of polymerase enzymes that can be used for PCR are thermostable polymerases, including but not limited to, *Thermus thermophilus* HB8; mutant *Thermus oshimai; Thermus scotoductus; Thermus thermophilus* 1B21; *Thermus thermophilus* GK24; *Thermus aquaticus* polymerase (AmpliTaq® FS or Taq (G46D; F667Y), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerase enzymes that can be used for PCR are non-thermostable polymerases, including, but are not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase.

In some embodiments, primer extension and amplification reactions comprise isothermal reactions. Non-limiting examples of isothermal amplification technologies are ligase chain reaction (LCR); transcription mediated amplification (TMA); nucleic acid sequence-based amplification (NASBA); signal mediated amplification of RNA technology (SMART); strand displacement amplification (SDA); thermophilic SDA; rolling circle amplification (RCA); loop-mediated isothermal amplification of DNA (LAMP); helicase-dependent amplification (HDA); single primer isothermal amplification (SPIA); and circular helicase-dependent amplification (cHDA).

In various embodiments of the aspects herein, a hot-start polymerase is used for extension and/or amplification. The term "hot-start" generally refers to a means of limiting the availability of an essential reaction component (e.g., a polymerase) when the reaction mixture is maintained at a first temperature (typically a lower temperature) until a second temperature (typically a higher temperature) is reached which allows the essential component to participate in the reaction. Hot-start reactions typically involve incubation at a first (e.g., lower) temperature and subsequent elevation to a second (e.g., higher) temperature which allows the desired reaction to take place. Activation of the hot start reaction can be achieved by incubating a reaction mixture at a temperature which is equal to or higher than the primer hybridization (annealing) temperature. Use of a temperature which is equal to or greater than the primer hybridization temperature can ensure primer binding specificity. The length of incubation required to recover enzyme activity depends on the temperature and pH of the reaction mixture and on the stability of the enzyme. A wide range of incubation conditions are usable; optimal conditions may be determined empirically for each reaction. The solutions can be optionally heated to and held at a first temperature for a first period of time suitable for hot-start activation of the nucleic acid polymerases.

Non-limiting exemplary hot start mechanisms include, but are not limited to, antibodies or combinations of antibodies that block nucleic acid polymerase activity at lower temperatures and which dissociate from the polymerase at elevated temperatures; affibodies or combinations of affibodies, sometimes referred to as antibody mimetics; oligonucleotides that block nucleic acid polymerase activity at lower temperatures and which dissociate from the polymerase at elevated temperatures; reversible chemical modification of the nucleic acid polymerase such that the nucleic acid polymerase activity is blocked at lower temperatures and the modifications reverse or dissociate at elevated temperatures; amino acid mutations of the nucleic acid polymerase that provide reduced activity at lower temperatures; nucleic acid polymerase fusion proteins including hyperstable DNA binding domains and topoisomerases; ligands that inhibit the nucleic acid polymerase in a temperature-dependent manner; single-stranded binding proteins that sequester primers at low temperatures; thermostable pyrophosphatase which hydrolyzes inorganic pyrophosphate at elevated temperatures; thermolabile blockers, such as a polymerase blocking protein; primer competitor sequences; modified primer constructs; modified primers that improve hybridization selectivity; primers with 3' modifications that are removable by 3'-5' exonuclease activity; primers with modified nucleobases that are removable by UV irradiation; primer modifications that are removable by thermal deprotection; or modification of the dNTPs with thermolabile modification groups. Agents that are used as hot start mechanisms, such as, but not limited to, antibodies, oligonucleotides, Affibodies, chemical modifications, etc., may be referred to as "hot start inhibitors."

In some embodiments, a hot start composition comprises an antibody specific for the polymerase. In some embodiments, a hot start composition comprises an antibody specific for the polymerase, which is bound to the polymerase. In some embodiments, a hot start composition comprises an inhibitor specific for the polymerase, which is bound to the polymerase. In some embodiments, the inhibitor comprises an Affibody. In some embodiments, the inhibitor comprises an oligonucleotide. In some embodiments, the inhibitor comprises a chemical modification. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MTDSCI; Minerva Biolabs GmbH; New England Biolabs; Novagen; Promega; QIAGEN; Roche Applied Science; Sigma-Aldrich; Stratagene; Takara Minis Bio; USB Corp.; Yorkshire Bioscience Ltd; and the like.

In some embodiments of any of the various aspects of the present disclosure, a primer may comprise one or more portions. For example, a primer may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

Non-limiting examples of next-generation sequencing methods are single-molecule real-time sequencing, ion semiconductor sequencing, pyrosequencing, sequencing by synthesis, sequencing by ligation, and chain termination. Sequencing adapters for flow cell attachment may comprise any suitable sequence compatible with next generation sequencing systems, e.g., 454 Sequencing, Ion Torrent Proton or PGM, and Illumina X10. Non-limiting examples of sequencing adapters for next generation sequencing methods include P5 and P7 adapters suitable for use with Illumina sequencing systems; TruSeq Universal Adapter; and TruSeq Indexed Adapter. In some embodiments, a sequencing adapter can be used to enrich, e.g., via amplification, such as polymerase chain reaction (PCR), for polynucleotides comprising the adapter sequence. Sequencing adapters can further comprise a barcode sequence and/or a sample index sequence.

In some embodiments, a primer comprises a barcode sequence. A barcode sequence refers to a known nucleic acid sequence that allows some feature of a polynucleotide with which the barcode is associated to be identified. Barcodes can each have a length within a range of 5 to 35 nucleotides, 6 to 30 nucleotides, or 8 to 20 nucleotides. In some embodiments, barcodes are at least 3, 4, 5, 6, 7, 8, 9, 10, 11, 12, 13, 14, or 15 nucleotides in length. In some embodiments, barcodes are less than 6 nucleotides in length. In some embodiments, barcodes associated with some target polynucleotides may be a different length than barcodes associated with other target polynucleotides. The melting temperatures of barcodes within a set can be within ±10° C. of one another, within ±5° C. of one another, or within ±2° C. of one another. Barcodes can be members of a minimally cross-hybridizing set. For example, the nucleotide sequence of each member of such a set can be sufficiently different from that of every other member of the set that no member can form a stable duplex with the complement of any other member under moderate or stringent hybridization conditions. The nucleotide sequence of each member of a minimally cross-hybridizing set can differ from those of every other member by at least two nucleotides. Some barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101: 11046; and Brenner (2004) Genome Biol. 5:240, each of which is herein incorporated in its entirety by reference.

Amplification products (also referred to as amplicons) produced according to methods herein can be analyzed by sequencing. A variety of sequencing methodologies are available for sequencing amplification products. In some embodiments, high-throughput sequencing methodologies are used. Non-limiting examples of sequencing methodologies that can be used include sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300 nucleotides or more in length. In some embodiments, sequencing comprises a sequencing-by-synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the $\alpha$ and $\beta$ phosphates of the triphosphate chain, releasing pyrophosphate. The presence of released pyrophosphate is then identified using a chemiluminescent enzyme reporter system that converts the pyrophosphate, with AMP, into ATP, and then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In some embodiments, the amplification products are sequenced to obtain haplotype information. Haplotype information can include haplotype phasing. In some embodiments, determining haplotype phasing comprises determining if a polynucleotide originated from a paternal chromosome or a maternal chromosome. In some embodiments, haplotype information can comprise haplotype construction or genetic phasing. Methods disclosed herein can be used for building diploid reference genomes.

In some embodiments, the amplification products are sequenced to detect a sequence variant, e.g., inversion, deletion, duplication, translocation, and rare somatic mutations, with respect to a reference sequence or in a background of no mutations. In some embodiments, the sequence variant is correlated with disease (e.g., cancer). In some embodiments, the sequence variant is not correlated with disease. In general, sequence variants for which there is statistical, biological, and/or functional evidence of association with a disease or trait are referred to as "causal genetic variants." A single causal genetic variant can be associated with more than one disease or trait. In some cases, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants have been reported. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Additional non-limiting examples of causal genetic variants are described in WO2014015084. Additional non-limiting examples of methods for the identification of rare sequence variants are described in WO2015089333.

In some embodiments of any of the various aspects of the present disclosure, amplification products are purified prior to sequencing. Amplification products can be purified by various methods. Amplification products may be purified to remove excess or unwanted reagents, reactants, or products. Amplification products may further be purified by size, sequence, or other physical or chemical characteristic. In some embodiments, amplicons may be subjected to size exclusion chromatography. In some embodiments, amplification products may be subjected to fragment excision from gels and gel filtration (e.g. to enrich for fragments larger than about 300, 400, 500, or more nucleotides in length); as well as SPRI beads (Agencourt AMPure XP) for size selection by fine-tuning the binding buffer concentration. For example, the use of 0.6× binding buffer during mixing with DNA fragments may be used to preferentially bind DNA fragments larger than about 500 base pairs (bp).

Embodiments of the disclosure provided herein can be used to identify a variety of sequence variants associated with one or more kinds of cancer. Suitable target sequences of oncological significance that find use in the methods of the disclosure include, but are not limited to, alterations in the TP53 gene, the ALK gene, the KRAS gene, the PIK3CA gene, the BRAF gene, the EGFR gene, and the KIT gene. A target sequence the may be specifically amplified, and/or specifically analyzed for sequence variants may be all or part of a cancer-associated gene. In some embodiments, one or more sequence variants are identified in the TP53 gene. TP53 is one of the most frequently mutated genes in human cancers, for example, TP53 mutations are found in 45% of ovarian cancers, 43% of large intestinal cancers, and 42% of cancers of the upper aerodigestive track (see e.g. M. Olivier, et, al. TP53Mutations in Human Cancers: Origins, Consequences, and Clinical Use. Cold Spring Harb Perspect Biol. 2010 January; 2(1). Characterization of the mutation status of TP53 can aid in clinical diagnosis, provide prognostic value, and influence treatment for cancer patients. For example, TP53 mutations may be used as a predictor of a poor prognosis for patients in CNS tumors derived from glial cells and a predictor of rapid disease progression in patients with chronic lymphocytic leukemia (see e.g. McLendon R E, et al. Cancer. 2005 Oct. 15; 1 04(8): 1693-9; Dicker F, et al. Leukemia. 2009 January; 23(1): 117-24). Sequence variation can occur anywhere within the gene. Thus, all or part of the TP53 gene can be evaluated herein. That is, as described elsewhere herein, when target specific components (e.g. target specific primers) are used, a plurality of TP53 specific sequences can be used, for example to amplify and detect fragments spanning the gene, rather than just one or more selected subsequences (such as mutation "hot spots") as may be used for selected targets. Alternatively, target-specific primers may be designed that hybridize upstream or downstream of one or more selected subsequences (such a nucleotide or nucleotide region associated with an increased rate of mutation among a class of subjects, also encompassed by the term "hot spot").

Additional non-limiting examples of genes associated with cancer, all or a portion of which may be analyzed for sequence variants according to a method described herein include, but are not limited to PTEN; ATM; ATR; EGFR; ERBB2; ERBB3; ERBB4; Notch 1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR; (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; and Ape.

Examples of cancers with which selected gene sequences may be associated include, without limitation, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof.

EXAMPLES

The following examples are given for the purpose of illustrating various embodiments of the disclosure and are not meant to limit the present disclosure in any fashion. The present examples, along with the methods described herein, are examples and are not intended as limitations on the scope of the disclosure.

Example 1: X1 and X2 Homodimer Transposome Complexes

To generate X1-ME containing transposome complexes, equal molar DNA oligos transposon X1-ME: GTAGGTGTGAGTGATGGTTGAGGTAGT-AGATGTGTATAAGAGACAG (SEQ ID NO: 1) and ME': (5phos)-CTGTCTCTTATACACATCT (SEQ ID NO: 2) were annealed in the presence of 1×STE (10 mM Tris pH 8.0, 50 mM NaCl, 1 mM EDTA) by incubating at 95° C. for 1 minute and then cooling down to room temperature. Double-stranded transposon was then incubated with Tn5 transposase at 1.2:1 molar ratio at room temperature for 30 minutes to form transposome complexes (Tn5-X1-ME).

To generate X2-ME containing transposome complexes, equal molar DNA oligos transposon X2-ME: GTGAGTGATGGTTGAGGTAGTGTGGAG-AGATGTGTATAAGAGACAG (SEQ ID NO: 3) and ME': (5phos)-CTGTCTCTTATACACATCT (SEQ ID NO: 2) were annealed in the presence of 1×STE (10 mM Tris pH 8.0, 50 mM NaCl, 1 mM EDTA) by incubating at 95° C. for 1 minute then cooling down to room temperature. Double-stranded transposon was then incubated with Tn5 transposase at 1.2:1 molar ratio at room temperature for 30 minutes to form transposome complexes (Tn5-X2-ME).

10 pg genomic DNA was incubated with transposome complex Tn5-X1-ME in the presence of 5 mM MgCl$_2$ at 55° C. for 15 minutes. 1 uL of 2 mg/ml protease was later added to the reaction. The reaction was then incubated at 50° C. for 10 minutes and then at 72° C. for 15 minutes.

In single primer pre-amplification, fragmented double-strand DNA was incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM primer: GTAGGTGTGAGTGATGGTT-GAGGTAGTAGATGTGTATAAGAGACAG (SEQ ID NO: 1). The reaction was subjected to the following conditions: 72° C. for 3 minutes; 98° C. for 2 minutes, followed by 16 cycles of 98° C. for 15 seconds and 72° C. for 3 minutes 30 seconds.

To perform a second tagmentation, preamplification product was then incubated with transposome complex Tn5-X2-ME in presence of MgCl$_2$ at 55° C. for 10 minutes. Second tagmenation product was then purified by DNA Clean & Concentrator-5 (Zymo Research). Then, fragmented double-strand DNA was incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM index primer mix. The reaction was subjected to the following conditions: 72° C. for 3 minutes; 98° C. for 2 minutes, followed by 8 cycles of 98° C. for 15 seconds, 63° C. 30 seconds and 72° C. for 3 minutes 30 seconds.

The resulting amplified product was purified to serve as library for sequencing on Illumina HiSeq X or NovaSeq sequencer for paired-end reads.

Example 2: X1 and X2 Homo- and Hetero-Dimer Transposome Complexes

To generate X1-ME transposome complexes, equal molar DNA oligos transposon X1-ME: GTAGGTGTGAGT-GATGGTTGAGGTAGT-AGATGTGTATAAGAGACAG (SEQ ID NO: 1) and ME': (5phos)-CTGTCTCTTATACA-CATCT (SEQ ID NO: 2) were annealed in presence of 1×STE (10 mM Tris pH 8.0, 50 mM NaCl, 1 mM EDTA) by incubating at 95° C. for 1 minute then cooling down to room temperature. Double-stranded transposon was then incubated with Tn5 transposase at 1.2:1 molar ratio at room temperature for 30 minutes to form transposome complexes (Tn5-X1-ME).

To generate X2-ME transposome complexes, equal molar DNA oligos transposon X2-ME: GTGAGTGATGGTT-GAGGTAGTGTGGAG-AGATGTGTATAAGAGACAG (SEQ ID NO: 3) and ME': (5phos)-CTGTCTCTTATACA-CATCT (SEQ ID NO: 2) were annealed in presence of 1×STE (10 mM Tris pH 8.0, 50 mM NaCl, 1 mM EDTA) by incubating at 95° C. for 1 minute then cooling down to room temperature. Double-stranded transposon was then incubated with Tn5 transposase at 1.2:1 molar ratio at room temperature for 30 minutes to form transposome complexes (Tn5-X2-ME).

10 pg genomic DNA was incubated with transposome complexes Tn5-X1-ME in the presence of 5 mM MgCl$_2$ at 55° C. for 15 minutes. 1 uL 2 mg/ml protease was later added to the reaction. The reaction was then incubated at 50° C. for 10 minutes then 72° C. for 15 minutes.

In single primer preamplification, fragmented double-strand DNA was incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM primer: GTAGGTGTGAGTGATGGTT-GAGGTAGTAGATGTGTATAAGAGACAG (SEQ ID NO: 1). The reaction was subjected to the following conditions: 72° C. for 3 minutes; 98° C. for 2 minutes, followed by 16 cycles of 98° C. for 15 seconds and 72° C. for 3 minutes 30 seconds.

To perform a second tagmentation, preamplification product was then incubated with transposome complexes Tn5-X1-ME and Tn5-X2-ME in the presence of MgCl$_2$ at 55° C. for 10 minutes. Second tagmentation product was then purified by DNA Clean & Concentrator-5 (Zymo Research). Fragmented double-strand DNA was incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM index primer mix. The reaction was subjected to the following conditions: 72° C. for 3 minutes; 98° C. for 2 minutes, followed by 8 cycles of 98° C. for 15 seconds, 63° C. 30 seconds and 72° C. for 3 minutes 30 seconds.

The resulting amplified product was purified to serve as library for sequencing on Illumina HiSeq X or NovaSeq sequencer for paired-end reads.

Example 3: Generating Identifiable Sense and Antisense Strands

To generate transposome complexes, equal molar DNA oligos transposon ME: AGATGTGTATAAGAGACAG (SEQ ID NO: 4) and ME': (5phos)-CTGTCTCTTATACA-CATCT (SEQ ID NO: 2) are annealed in the presence of 1×STE (10 mM Tris pH 8.0, 50 mM NaCl, 1 mM EDTA) by incubating at 95° C. for 1 minute then cooling down to room temperature. Double-stranded transposon are then incubated with Tn5 transposase at 1.2:1 molar ratio at room temperature for 30 minutes to form transposome complex Tn5-ME.

10 pg genomic DNA is incubated with transposome complex Tn5-ME in the presence of 5 mM MgCl$_2$ at 55° C. for 15 minutes. 1 uL 2 mg/ml protease is added to the reaction followed by incubation at 50° C. for 10 minutes then 72° C. for 15 minutes.

In a first primer extension, fragmented double-strand DNA is incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM primer X1-ME: GTAGGTGTGAGTGATGGTT-GAGGTAGTAGATGTGTATAAGAGACAG (SEQ ID NO: 1). The reaction is then subjected to the following conditions: 72° C. for 3 minutes; 98° C. for 2 minutes, followed by 72° C. for 3 minutes 30 seconds. Exonuclease I is then added to the reaction to digest excess X1-ME oligo. The reaction is incubated at 80° C. for 15 minutes.

To perform a second primer extension, prior product is incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM primer X2-ME: GTGAGTGATGGTTGAGGTAGTGTG-GAG-AGATGTGTATAAGAGACAG (SEQ ID NO: 3). The reaction is subjected to the following conditions: 98° C. for 2 minutes, followed by 72° C. for 3 minutes 30 seconds. Exonuclease I is then added to the reaction to digest excess X2-ME oligo followed by 80° C. incubation for 15 minutes.

For indexing PCR, primer extension product is incubated in a 30 uL reaction with 1×Q5 Reaction Buffer, 0.02 U/uL Q5 Hot Start High-Fidelity DNA Polymerase (New England BioLabs Inc), 200 uM dNTPs, and 0.5 uM index primer mix. The reaction is subjected to the following conditions: 72° C. for 3 minutes; 98° C. for 2 minutes, followed by 8 cycles of 98° C. for 15 seconds, 63° C. 30 seconds and 72° C. for 3 minutes 30 seconds.

The resulting amplified product is purified to serve as library for sequencing on Illumina HiSeq X or NovaSeq sequencer for paired-end reads.

Example 4: Tagmentation with an Asymmetric Mixture of Transposome Complexes

To generate transposome complexes, equal molar DNA oligos transposon X1-ME: GTAGGTGTGAGTGATGGTT-GAGGTAGT-AGATGTGTATAAGAGACAG (SEQ ID NO: 1) and ME': (5phos)-CTGTCTCTTATACACATCT (SEQ ID NO: 2) were annealed in the presence of 1×STE (10 mM Tris pH 8.0, 50 mM NaCl, 1 mM EDTA) by incubating at 95° C. for 1 minute then cooling down to room temperature. Double-stranded transposon was then incubated with Tn5 transposase at 1.2:1 molar ratio at room temperature for 30 minutes to form transposome complexes Tn5-X1-ME.

To generate transposome complexes, equal molar DNA oligos transposon X2-ME: GTGAGTGATGGTT-GAGGTAGTGTGGAG-AGATGTGTATAAGAGACAG (SEQ ID NO: 3) and ME': (5phos)-CTGTCTCTTATACA-CATCT (SEQ ID NO: 2) were annealed in the presence of 1×STE (10 mM Tris pH 8.0, 50 mM NaCl, 1 mM EDTA) by incubating at 95° C. for 1 minute then cooling down to room temperature. Double-stranded transposon was then incubated with Tn5 transposase at 1.2:1 molar ratio at room temperature for 30 minutes to form transposome complex Tn5-X2-ME. Transposome complexes Tn5-X1-ME and Tn5-X2-ME were mixed at 1:9 molar ratio to form a mixture of asymmetric transposome complexes.

10 pg genomic DNA was incubated with the asymmetric transposome complexes Tn5-X1-ME:Tn5-X2-ME in the presence of 5 mM $MgCl_2$ at 55° C. for 15 minutes. 1 uL 2 mg/ml protease was later added to reaction followed by incubation at 50° C. for 10 minutes, then 72° C. for 15 minutes.

In a single primer preamplification, fragmented double-strand DNA was incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM primer: GTAGGTGTGAGTGATGGTT-GAGGTAGTAGATGTGTATAAGAGACAG (SEQ ID NO: 1). The reaction was subjected to the following conditions: 72° C. for 3 minutes; 98° C. for 2 minutes, followed by 16 cycles of 98° C. for 15 seconds and 72° C. for 3 minutes 30 seconds.

To perform a second tagmentation, preamplification product was then incubated with transposome complex Tn5-X1-ME and Tn5-X2-ME in presence of $MgCl_2$ at 55° C. for 10 minutes. Second tagmenation product was then purified by DNA Clean & Concentrator-5 (Zymo Research). Fragmented double-strand DNA was incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM index primer mix. The reaction was subjected to the following conditions: 72° C. for 3 minutes; 98° C. for 2 minutes, followed by 8 cycles of 98° C. for 15 seconds, 63° C. 30 seconds and 72° C. for 3 minutes 30 seconds.

The resulting amplified product was purified to serve as a library for sequencing on Illumina HiSeq X or NovaSeq sequencer for paired-end reads.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXEMPLARY EMBODIMENTS

Among the exemplary embodiments are: 1. Methods of characterizing a polynucleotide in a sample, comprising: (a) contacting a double-stranded polynucleotide in a sample with a first set of transposome complexes, said first set comprising transposome complexes having a first transposon sequence, to generate a first plurality of overhang fragments that comprise the first transposon sequence at a 5' end; (b) subjecting said first plurality of overhang fragments to an extension reaction to generate a first plurality of blunt-ended fragments; (c) conducting a primer-directed extension reaction with a primer comprising the first transposon sequence or a portion thereof to generate copies of the first plurality of blunt-ended fragments or fragments thereof; (d) contacting said first plurality of blunt-ended fragments or fragments thereof with a second set of transposome complexes, said second set comprising transposome complexes having a second transposon sequence, to generate a second plurality of overhang fragments that comprise the second transposon sequence at a 5' end; (e) subjecting said second plurality of overhang fragments to an additional extension reaction to generate a second plurality of blunt-ended fragments; and (f) generating sequence reads from said second plurality of blunt-ended fragments or derivatives thereof, thereby characterizing the double-stranded polynucleotide in the sample. 2. The methods of embodiment 1, wherein said first transposon sequence and said second transposon sequence are not identical. 3. The methods of embodiment 1, wherein said second set further comprises transposome complexes having the first transposon sequence. 4. The methods of embodiment 1, wherein said second set further comprises transposome complexes having a third transposon sequence. 5. Methods of characterizing a polynucleotide in a sample, comprising: (a) contacting a double-stranded polynucleotide in a sample with a first set of transposome complexes, individual transposome complexes of said first set comprising a first transposon sequence, to generate a first plurality of overhang fragments that comprise the first transposon sequence at a 5' end; (b) subjecting said first plurality of overhang fragments to an extension reaction to generate a first plurality of blunt-ended fragments; (c) conducting a primer-directed extension reaction with a primer comprising the first transposon sequence or a portion thereof to generate copies of the first plurality of blunt-ended fragments or fragments thereof; (d) contacting said first plurality of blunt-ended fragments or fragments thereof with a second set of transposome complexes, individual transposome complexes of said second set comprising a second transposon sequence, to generate a second plurality of overhang fragments that comprise the second transposon sequence at a 5' end, wherein the first set of transposome complexes and the second set of transposome complexes are different in that: (i) transposon sequences comprised therein are distinct between the first and the second sets of transposome complexes; and/or (ii) one set of the transposome complexes utilized in step (a) or (d) are homodimer transposomes and one other set of the transposome complexes utilized are heterodimer transposomes; (e) subjecting said second plurality of overhang fragments to an additional extension reaction to generate a second plurality of blunt-ended fragments; and (f) generating sequence reads from said second plurality of blunt-ended fragments or derivatives thereof, thereby characterizing the double-stranded polynucleotide in the sample. 6. The methods of embodiment 5, wherein the first set of transposome complexes and the second set of transposome complexes are different in that transposon sequences comprised therein are distinct between the first and the second sets of the transposome complexes. 7. The methods of embodiment 5, wherein the first set of transposome complexes and the second set of transposome complexes are different in that one set of the transposome complexes utilized in step (a) or (d) are homodimer transposomes and one other set of transposome complexes utilized are heterodimer transposomes. 8. The methods of embodiment 5, wherein step (d) comprises contacting said first plurality of blunt-ended fragments or fragments thereof with at least two additional sets of transposome complexes, wherein individual sets of said additional sets of transposome complexes comprise homodimer transposomes, and wherein transposon sequences across said individual sets are unique. 9. The methods of any one of embodiments 1 to 8, wherein said double-stranded polynucleotide comprises genomic DNA. 10. The methods of embodiment 9, wherein said genomic DNA is from a single cell. 11. The method of any of the preceding embodiments, wherein said double-stranded polynucleotide comprises a chromosome. 12. The methods of any of the preceding embodiments, wherein said double-stranded polynucleotide is from a single cell. 13. The methods of any of the preceding embodiments, wherein characterizing said double-stranded polynucleotide yields haplotype information. 14. The methods of any of the preceding embodiments, wherein characterizing said double-stranded polynucleotide comprises identifying a structural variation in said polynucleotide, wherein said structural variation is a copy number variation (CNV), an insertion, a deletion, a translocation, a retrotransposon, an inversion, a rearrangement, a repeat expansion, or a duplication. 15. The methods of any of the preceding embodiments, wherein the double-stranded polynucleotide is at least about 1 megabase (Mb) in length. 16. The methods of any of the preceding embodiments, wherein said first plurality of blunt-ended fragments comprises fragments of at least about 500 bases in length. 17. The methods of any of the preceding embodiments, wherein said second plurality of blunt-ended fragments comprises fragments of at least about 100 bases in length. 18. The methods of any of the preceding embodiments, wherein individual single-stranded polynucleotides of said first plurality of blunt-ended fragments form a stem-loop structure. 19. The methods of embodiment 18, wherein said stem-loop structure comprises a stem of at least 10 base pairs in length. 20. The methods of embodiment 18, wherein the stem of said stem-loop structure has a melting temperature (Tm) of at least 50° C. 21. The methods of any of the preceding embodiments, further comprising attaching sequencing adaptors to said second plurality of blunt-ended fragments to yield said derivatives thereof 22. The methods of any of the preceding embodiments, wherein individual transposome complexes of said first set and/or said second set comprise a transposase selected from Tn transposase, MuA transposase, and Vibhar transposase. 23. The methods of embodiment 22, wherein said transposase is a Tn transposase selected from Tn3, Tn5, Tn7, and Tn10. 24. Methods of identifying a low frequency allele, comprising: (a) contacting a double-stranded polynucleotide with transposome complexes, individual transposome complexes comprising a transposon sequence, to generate a plurality of overhang fragments that comprise the transposon sequence at a 5' end; (b) subjecting said plurality of overhang fragments to an extension reaction to generate a plurality of blunt-ended fragments; (c) conducting a first primer-directed extension reaction with a primer comprising the transposon sequence or a portion thereof and a first barcode sequence (X1) to generate a first plurality of barcoded polynucleotides comprising the first barcode sequence (X1) at a 5' end; (d) conducting a second primer-directed extension with a primer comprising the transposon sequence or a portion thereof and a second barcode sequence (X2) to generate a second plurality of barcoded polynucleotides comprising the second barcode sequence (X2) at a 5' end and a reverse complement of the first barcode sequence (X1') at a 3' end; (e) generating sequence reads from said second plurality of barcoded polynucleotides or derivatives thereof to yield a plurality of sequence reads; and (f) identifying a low frequency allele in said double-stranded polynucleotide when said low frequency allele occurs in sequence reads of both a sense strand and an antisense strand of said double-stranded polynucleotide, wherein (i) sequence reads comprising, from 5' end to 3' end, (a) X2, the sense strand sequence, and X1' or (b) X1, the antisense strand sequence, and a reverse complement of X2 (X2'), are identified as originating from the sense strand of said double-stranded polynucleotide, and (ii) sequence reads comprising, from a 5' end to 3' end, (a) X1, the sense strand sequence, and X2' or (b) X2, the antisense strand sequence, and X1', are identified as originating from the antisense strand of said double-stranded polynucleotide. 25. Methods of identifying a sequence variant, comprising: (a) contacting a double-stranded polynucleotide with transposome complexes, individual transposome complexes comprising a transposon sequence, to generate a plurality of overhang fragments that comprise the transposon sequence at a 5' end; (b) subjecting said plurality of overhang fragments to an extension reaction to generate a plurality of blunt-ended fragments; (c) conducting a first primer-directed extension reaction with a primer comprising the transposon sequence or a portion thereof and a first barcode sequence (X1) to generate a first plurality of barcoded polynucleotides comprising the first barcode sequence (X1) at a 5' end; (d) conducting a second primer-directed extension with a primer comprising the transposon sequence or a portion thereof and a second barcode sequence (X2) to generate a second plurality of barcoded polynucleotides comprising the second barcode sequence (X2) at a 5' end and a reverse complement of the first barcode sequence (X1') at a 3' end; (e) generating sequence reads from said second plurality of barcoded polynucleotides or derivatives thereof to yield a plurality of sequence reads; and (f) identifying a sequence variant in said double-stranded polynucleotide compared to a reference sequence when said sequence variant occurs in sequence reads of both a sense strand and an antisense strand of said double-stranded polynucleotide, wherein (i) sequence reads comprising, from 5' end to 3' end, (a) X2, the sense strand sequence, and X1' or (b) X1, the antisense strand sequence, and a reverse complement of X2 (X2'), are identified as originating from the sense strand of said double-stranded polynucleotide, and (ii) sequence reads comprising, from a 5' end to 3' end, (a) X1, the sense strand sequence, and X2' or (b) X2, the antisense strand sequence, and X1', are identified as originating from the antisense strand of said double-stranded polynucleotide. 26. The methods of embodiment 24 or 25, wherein said double-stranded polynucleotide comprises genomic DNA. 27. The methods of embodiment 26, wherein said genomic DNA is from a single cell. 28. The methods of embodiment 24 or 25, wherein the double-stranded polynucleotide comprises cell-free DNA. 29. The methods of any one of embodiments 24 to 28, wherein the double-stranded polynucleotide is at least 1 megabase (Mb) in length. 30. The methods of any one of embodiments 24 to 29, wherein said plurality of blunt-ended fragments comprises fragments at least 100 bases in length. 31. The methods of any one of embodiments 24 to 30, further comprising attaching sequencing adaptors to said second plurality of barcoded polynucleotides to yield said derivatives thereof 32. The methods of any one of embodiments 24 to 31, wherein individual transposome complexes comprise a transposase selected from Tn transposase, MuA transposase, and Vibhar transposase. 33. The methods of embodiment 32, wherein said transposase is a Tn transposase selected from Tn3, Tn5, Tn7, and Tn10. 34. The methods of embodiment 24, wherein an allele frequency of said low frequency allele in a population is less than 5%. 35. The methods of embodiment 24, wherein said low frequency allele is detected with an accuracy of at least 85%. 36. The methods of embodiment 25, wherein said sequence variant represents less than 5% of double-stranded polynucleotides in a nucleic acid sample. 37. The methods of embodiment 25, wherein said sequence variant is detected with an accuracy of at least 85%. 38. The methods of embodiment 36, wherein said nucleic acid sample comprises cell-free polynucleotides. 39. The methods of embodiment 36, wherein said nucleic acid sample is from a single cell. 40. Methods of selectively sampling a subset of regions of a polynucleotide, comprising: (a) contacting a double-stranded polynucleotide with a first set of transposome complexes to generate a first plurality of overhang fragments that comprise a first transposon sequence or a second transposon sequence at the 5' end, wherein said first set of transposome complexes comprises a mixture of (i) homodimer transposases comprising the first transposon sequence, and (ii) homodimer transposases comprising the second transposon sequence; (b) subjecting said first plurality of overhang fragments to an extension reaction to generate a first plurality of blunt-ended fragments; (c) conducting a primer-directed extension reaction with a primer comprising the first transposon sequence or a portion thereof to selectively generate copies of a subset of the first plurality of blunt-ended fragments comprising the first transposon sequence or fragments thereof; (d) contacting said first plurality of blunt-ended fragments comprising the first transposon sequence or fragments thereof with a second set of transposome complexes to generate a second plurality of overhang fragments, wherein said second set of transposome complexes comprises (i) a plurality of homodimer transposases, or (ii) a plurality of heterodimer transposases; (e) subjecting said second plurality of overhang fragments to an additional extension reaction to generate a second plurality of blunt-ended fragments; and (f) generating sequence reads from said second plurality of blunt-ended fragments or derivatives thereof, thereby selectively sampling a subset of regions of the double-stranded polynucleotide. 41. The methods of embodiment 40, wherein the second set of transposome complexes comprises a plurality of homodimer transposases. 42. The methods of embodiment 40, wherein the second set of transposome complexes comprises a plurality of heterodimer transposases. 43. The methods of any one of embodiments 40 to 42, wherein in said mixture of (i) homodimer transposases comprising the first transposon sequence, and (ii) homodimer transposases comprising the second transposon sequence, (i) and (ii) are present at a molar ratio of about 1:9. 44. The methods of any one of embodiments 40 to 43, wherein in said mixture of (i) homodimer transposases comprising the first transposon sequence, and (ii) homodimer transposases comprising the second transposon sequence, (i) and (ii) are present at a molar ratio not equal to 1:1. 45. The methods of any one of embodiments 40 to 44, wherein said mixture of (a) further comprises (iii) heterodimer transposases comprising the first transposon sequence and the second transposon sequence. 46. The methods of embodiment 45, wherein in said mixture of (i) homodimer transposases comprising the first transposon sequence, (ii) homodimer transposases comprising the second transposon sequence, and (iii) heterodimer transposases comprising the first transposon sequence and the second transposon sequence, a molar concentration of (i) is less than that of (ii) and (iii). 47. The methods of embodiment 45, wherein in said mixture of (i) homodimer transposases comprising the first transposon sequence, (ii) homodimer transposases comprising the second transposon sequence, and (iii) heterodimer transposases comprising the first transposon sequence and the second transposon sequence, a molar concentration of (ii) is less than that of (i) and (iii). 48. The methods of embodiment 45, wherein in said mixture of (i) homodimer transposases comprising the first transposon sequence, (ii) homodimer transposases comprising the second transposon sequence, and (iii) heterodimer transposases comprising the first transposon sequence and the second transposon sequence, a molar concentration of (iii) is less than that of (i) and (ii). 49. The methods of any one of embodiments 40 to 48, wherein said first plurality of overhang fragments comprises (i) fragments comprising the first transposon sequence, (ii) fragments comprising the second transposon sequence, and (iii) fragments comprising both the first and second transposon sequence, and wherein a molar concentration of (i) is less than that of (ii) and (iii). 50. The methods of any one of embodiments 40 to 49, wherein said double-stranded polynucleotide comprises genomic DNA. 51. The methods of embodiment 50, wherein said genomic DNA is from a single cell. 52. The method of any one of embodiments 40 to 51, wherein said double-stranded polynucleotide comprises a chromosome. 53. The methods of any one of embodiments 40 to 52, wherein said double-stranded polynucleotide is from a single cell. 54. The methods of any one of embodiments 40 to 53, wherein said double-stranded polynucleotide is at least 1 megabase (Mb) in length. 55. The methods of any one of embodiments 40 to 54, wherein said first plurality of blunt-ended fragments comprises fragments at least 500 bases in length. 56. The methods of any one of embodiments 40 to 55, wherein said second plurality of blunt-ended fragments comprises fragments at least 100 bases in length. 57. The methods of any one of embodiments 40 to 56, wherein single-stranded polynucleotides of said first plurality of blunt-ended fragments comprising (i) the first transposon sequence at a 5' end and a reverse complement of the first transposon sequence at a 3' end, or (ii) the second transposon sequence at a 5' end and a reverse complement of the second transposon sequence at a 3' end form a stem-loop structure. 58. The methods of embodiment 57, wherein said stem-loop structure comprises a stem of at least 10 base pairs in length. 59. The methods of embodiment 57, wherein the stem of said stem-loop structure has a melting temperature (Tm) of at least 50° C. 60. The methods of any one of embodiments 40 to 59, further comprising attaching sequencing adaptors to said second plurality of blunt-ended fragments to yield said derivatives. 61. The methods of any one of embodiments 40 to 60, wherein individual transposome complexes of said first set and/or said second set comprise a transposase selected from Tn transposase, MuA transposase, and Vibhar transposase. 62. The methods of embodiment 61, wherein said transposase is a Tn transposase selected from Tn3, Tn5, Tn7, and Tn10. 63. Compositions comprising a mixture of (i) homodimer transposases comprising a first transposon sequence and (ii) homodimer transposases comprising a second transposon sequence. 64. The compositions of embodiment 63, wherein (i), and (ii), are present at a molar ratio of about 1:9. 65. The compositions of embodiment 63, wherein (i), and (ii), are present at a molar ratio not equal to 1:1. 66. The compositions of embodiment 63, further comprising (iii) heterodimer transposases comprising the first transposon sequence and the second transposon sequence. 67. The compositions of embodiment 66, wherein a molar concentration of (i) is less than that of (ii) and (iii). 68. The compositions of embodiment 63, wherein a molar concentration of (ii) is less than that of (i) and (iii). 69. The compositions of embodiment 63, wherein a molar concentration of (iii) is less than that of (i) and (ii). 70. Reaction mixtures comprising: (a) a mixture of (i) homodimer transposases comprising a first transposon sequence and (ii) homodimer transposases comprising a second transposon sequence; and (b) a double-stranded polynucleotide comprising genomic DNA. 71. The reaction mixtures of embodiment 70, further comprising (iii) heterodimer transposases comprising the first transposon sequence and the second transposon sequence. 72. The reaction mixtures of embodiment 70, wherein said genomic DNA is from a single cell. 73. The reaction mixtures of embodiment 70, wherein said genomic DNA is a single chromosome. 74. Kits comprising: (a) a first set of transposome complexes, individual transposome complexes of said first set comprising a first transposon sequence; (b) a primer comprising the first transposon sequence or a portion thereof; (c) a second set of transposome complexes, individual transposome complexes of said second set comprising a second transposon sequence; and (d) instructions for practicing method of embodiment 1 or embodiment 5, wherein the first set of transposome complexes and the second set of transposome complexes are different in that: (i) transposon sequences comprised therein are distinct between the first and the second sets of transposome complexes; and/or (ii) one set of the transposome complexes utilized in step (a) or (d) of the method of embodiment 1 are homodimer transposomes and one other set of the transposome complexes utilized are heterodimer transposomes. 75. Kits comprising: (a) transposome complexes, individual transposome complexes comprising a transposon sequence; (b) a first primer comprising the transposon sequence or a portion thereof and a first barcode sequence (X1); (c) a second primer comprising the transposon sequence or a portion thereof and a second barcode sequence (X2); and (d) instructions for practicing method of embodiment 24 or 25. 76. Kits comprising: (a) a first set of transposome complexes comprising: (i) homodimer transposases comprising a first transposon sequence, (ii) homodimer transposases comprising a second transposon sequence, and optionally (iii) heterodimer transposases comprising the first transposon sequence and the second transposon sequence; (b) a primer comprising the first transposon sequence or a portion thereof; (c) a second set of transposome complexes comprising: (i) a plurality of homodimer transposases, or (ii) a plurality of heterodimer transposases; and (d) instructions for practicing method of embodiment 40.

---

What is claimed is:

1. A method for characterizing a polynucleotide, comprising:
   (a) contacting a double-stranded polynucleotide in a sample with a first set of transposome complexes, said first set comprising transposome complexes having a first transposon sequence, to generate a first plurality of overhang fragments that comprise the first transposon sequence at a 5' end, wherein said first set of transposome complexes comprises homodimer transposomes and said double-stranded polynucleotide is from a single cell;
   (b) subjecting said first plurality of overhang fragments to a first extension reaction to generate a first plurality of blunt-ended fragments;
   (c) conducting a primer-directed extension reaction with a primer comprising the first transposon sequence or a portion thereof to generate copies of the first plurality of blunt-ended fragments or fragments thereof;
   (d) contacting said first plurality of blunt-ended fragments or fragments thereof with a second set of transposome complexes, said second set comprising transposome complexes having a second transposon sequence, to generate a second plurality of overhang fragments that comprise the second transposon sequence at a 5' end;
   (e) subjecting said second plurality of overhang fragments to a second extension reaction to generate a second plurality of blunt-ended fragments; and
   (f) generating sequence reads from said second plurality of blunt-ended fragments or derivatives thereof, thereby characterizing the double-stranded polynucleotide in the sample.

2. The method of claim 1, wherein said first transposon sequence and said second transposon sequence are not identical.

3. The method of claim 1, wherein said second set further comprises transposome complexes having the first transposon sequence.

4. The method of claim 1, wherein said second set further comprises transposome complexes having a third transposon sequence.

5. The method of claim 1, wherein said double-stranded polynucleotide comprises genomic DNA.

6. The method of claim 1, wherein characterizing said double-stranded polynucleotide yields haplotype information.

7. The method of claim 1, wherein characterizing said double-stranded polynucleotide comprises identifying a structural variation in said polynucleotide, wherein said structural variation is a copy number variation (CNV), an insertion, a deletion, a translocation, a retrotransposon, an inversion, a rearrangement, a repeat expansion, or a duplication.

8. The method of claim 1, wherein the double-stranded polynucleotide is at least about 1 megabase (Mb) in length.

9. The method of claim 1, wherein said second plurality of blunt-ended fragments comprises fragments of at least about 100 bases in length.

10. The method of claim 1, wherein individual single-stranded polynucleotides of said first plurality of blunt-ended fragments form a stem-loop structure.

11. The method of claim 10, wherein said stem-loop structure comprises a stem of at least 10 base pairs in length.

12. The method of claim 10, wherein the stem of said stem-loop structure has a melting temperature (Tm) of at least 50° C.

13. The method of claim 1, further comprising attaching sequencing adaptors to said second plurality of blunt-ended fragments to yield said derivatives thereof.

14. The method of claim 1, wherein individual transposome complexes of said first set and/or said second set comprise a transposase selected from Tn transposase, MuA transposase, and Vibhar transposase.

15. The method of claim 14, wherein said transposase is a Tn transposase selected from Tn3, Tn5, Tn7, and Tn10.

16. A method for characterizing a polynucleotide, comprising:
   (a) contacting a double-stranded polynucleotide in a sample with a first set of transposome complexes, individual transposome complexes of said first set comprising a first transposon sequence, to generate a first plurality of overhang fragments that comprise the first transposon sequence at a 5' end, wherein said first set of transposome complexes comprises homodimer transposomes and said double-stranded polynucleotide is from a single cell;
   (b) subjecting said first plurality of overhang fragments to a first extension reaction to generate a first plurality of blunt-ended fragments;
   (c) conducting a primer-directed extension reaction with a primer comprising the first transposon sequence or a portion thereof to generate copies of the first plurality of blunt-ended fragments or fragments thereof;
   (d) contacting said first plurality of blunt-ended fragments or fragments thereof with a second set of transposome complexes, individual transposome complexes of said second set comprising a second transposon sequence, to generate a second plurality of overhang fragments that comprise the second transposon sequence at a 5' end, wherein the first set of transposome complexes and the second set of transposome complexes are different in that:
  (i) transposon sequences comprised therein are distinct between the first and the second sets of transposome complexes; and/or
  (ii) one set of the transposome complexes utilized in step (a) or (d) are homodimer transposomes and one other set of the transposome complexes utilized are heterodimer transposomes;
(e) subjecting said second plurality of overhang fragments to a second extension reaction to generate a second plurality of blunt-ended fragments; and
(f) generating sequence reads from said second plurality of blunt-ended fragments or derivatives thereof, thereby characterizing the double-stranded polynucleotide in the sample.

17. The method of claim 16, wherein the first set of transposome complexes and the second set of transposome complexes are different in that transposon sequences comprised therein are distinct between the first and the second sets of the transposome complexes.

18. The method of claim 16, wherein the first set of transposome complexes and the second set of transposome complexes are different in that one set of the transposome complexes utilized in step (a) or (d) are homodimer transposomes and one other set of transposome complexes utilized are heterodimer transposomes.

19. The method of claim 16, wherein step (d) comprises contacting said first plurality of blunt-ended fragments or fragments thereof with at least two additional sets of transposome complexes, wherein each set of said additional sets of transposome complexes comprises homodimer transposomes, and wherein transposon sequences across said individual sets are unique.

* * * * *